(12) United States Patent
Hirschman et al.

(10) Patent No.: US 6,743,202 B2
(45) Date of Patent: Jun. 1, 2004

(54) ENCODING OF SYRINGE INFORMATION

(75) Inventors: Alan D. Hirschman, Glenshaw, PA (US); Arthur E. Uber, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 09/887,619

(22) Filed: Jun. 22, 2001

(65) Prior Publication Data

US 2001/0034506 A1 Oct. 25, 2001

Related U.S. Application Data

(60) Division of application No. 09/333,101, filed on Jun. 15, 1999, now abandoned, which is a continuation-in-part of application No. 09/097,412, filed on Jun. 15, 1998, now abandoned.

(51) Int. Cl.[7] .............................................. A61M 37/00
(52) U.S. Cl. ....................... 604/131; 604/151
(58) Field of Search ................. 604/131, 151, 604/153, 154, 152, 218, 227, 228, 207, 189, 208, 246, 118, 121; 120/DIG. 1; 340/571, 572.1, 572.5, 572.7, 572.8

(56) References Cited

U.S. PATENT DOCUMENTS

| 3,701,345 A | 10/1972 | Heilman et al. |
| 4,006,736 A | 2/1977 | Kranys et al. |
| 4,278,086 A | 7/1981 | Hodgins et al. |
| 4,650,475 A | 3/1987 | Smith et al. |
| 4,853,521 A | 8/1989 | Claeys et al. |
| 4,897,789 A | 1/1990 | King et al. |
| 4,950,246 A | 8/1990 | Muller |
| 4,976,696 A | 12/1990 | Sanderson et al. |
| 4,978,335 A | 12/1990 | Arthur, III |
| 5,176,502 A | 1/1993 | Sanderson et al. |
| 5,295,967 A | 3/1994 | Rondelet et al. |
| 5,300,042 A | 4/1994 | Kossoff et al. |
| 5,383,858 A * | 1/1995 | Reilly et al. ................. 604/152 |
| 5,449,344 A | 9/1995 | Taylor et al. |
| 5,509,905 A | 4/1996 | Michel |
| 5,569,212 A | 10/1996 | Brown |
| 5,593,390 A | 1/1997 | Castellano et al. |
| 5,628,309 A * | 5/1997 | Brown ........................ 128/632 |
| 5,651,775 A | 7/1997 | Walker et al. |
| 5,704,922 A * | 1/1998 | Brown ........................ 604/207 |
| 5,739,508 A | 4/1998 | Uber, III |
| 5,882,338 A * | 3/1999 | Gray .......................... 604/131 |
| 6,019,745 A * | 2/2000 | Gray .......................... 604/131 |
| 6,036,101 A * | 3/2000 | Hass et al. .................. 235/492 |

FOREIGN PATENT DOCUMENTS

| EP | 0 654 279 | 5/1995 |
| EP | 0 702 966 | 3/1996 |
| FR | 2 592 307 | 7/1987 |
| JP | 62-82352 * | 4/1987 .................. 73/602 |
| WO | WO 92/12402 | 7/1992 |
| WO | WO 93/02720 | 2/1993 |
| WO | WO 94/25089 * | 11/1994 .......... A61M/5/145 |

OTHER PUBLICATIONS

International Search Report for PCT Application No. PCT/US99/13360; from corresponding original US filing.

* cited by examiner

Primary Examiner—Brian L. Casler
Assistant Examiner—Jennifer Maynard
(74) Attorney, Agent, or Firm—Gregory L. Bradley

(57) ABSTRACT

Apparatuses for sharing information on syringe configuration between syringes and injector systems comprise a storage system to store encoded information on syringe configuration. The encoded information is readable by a detection circuit in an injector. In one embodiment, the storage system is an electronic storage system in which information relevant to the syringe configuration is encoded. A method comprises the step of conveying syringe configuration information to a detector in an injector for use with the syringe.

22 Claims, 27 Drawing Sheets

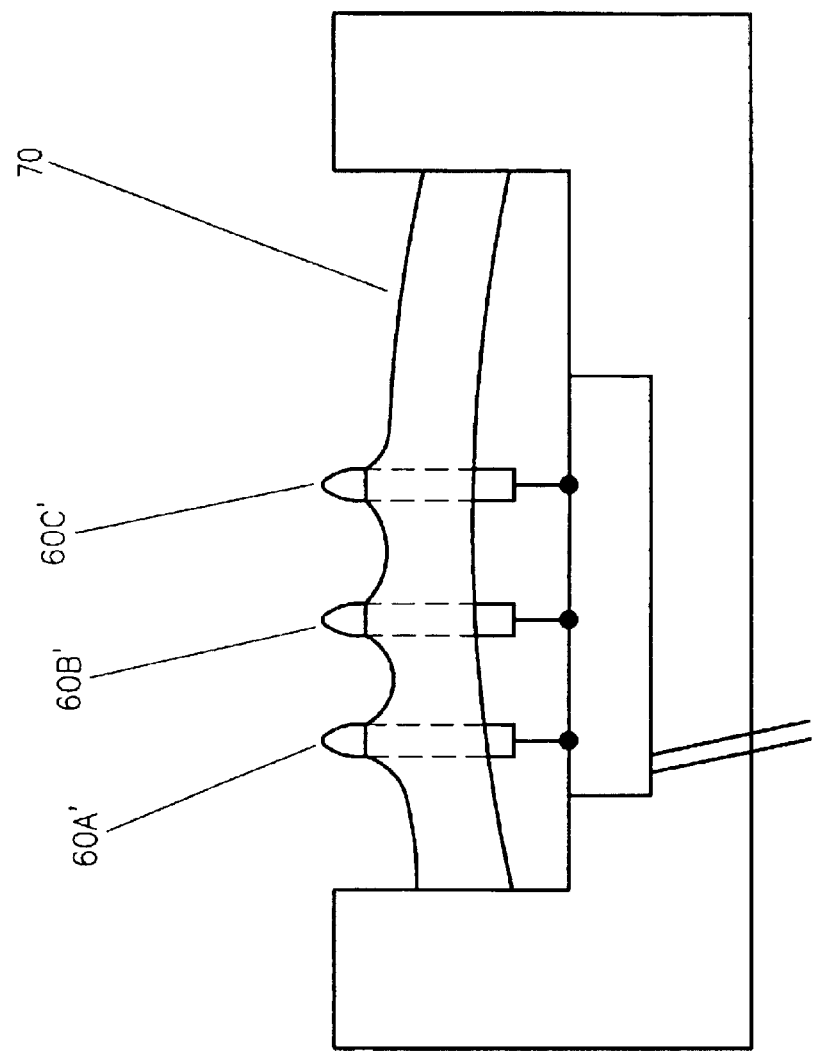

ENCODING OF SYRINGE INFORMATION

CROSS-REFERENCE TO RELATED APPLICATIONS

The present application is a divisional of application Ser. No. 09/333,101, filed on Jun. 15, 1999, abandoned, which is a continuation-in-part of application Ser. No. 09/097,412, filed on Jun. 15, 1998, abandoned, the disclosures of which are incorporated herein by reference.

BACKGROUND OF THE INVENTION

The present invention relates to apparatuses and methods for injecting fluid into a patient, and, more particularly, to apparatuses and methods for injecting fluid into a patient in which syringe information relevant to the injection procedure is encoded and shared with an injector.

The parameters of an injection procedure, such as the injection of contrast agents into a patient, include, for example, fluid volume available for delivery, flow rate, fluid pressure, and limits of piston travel. Injection parameters are determined by several variables, including, for example, syringe diameter, syringe length and fluid composition.

To program an injection procedure, some or all of the above injection parameters and variables, for example, must be input into the injector. In current injector systems, syringe size is input into an injector either (1) manually by an operator who enters the syringe size or syringe type into the injector software, or (2) automatically by means of switches on the injector head which are mechanically coupled to raised or sunken elements on the syringe barrel. Constraints on mechanical and electrical design, however, limit the number of such automatic detection switches. Indeed, only limited syringe configurations are automatically detected with present systems. (As used herein, the terms "syringe configuration" or "syringe information" encompasses all information about a particular syringe, including, but not limited to, information about the mechanical properties of a syringe (for example, length, diameter, available volume, pressure limitations, expiration date, prior use, and manufacturer) as well as information about the contents of the syringe (for example, fluid volume, expiration date, manufacturer and composition).

With the increasing variety of syringes and fluids contained therein, and especially prefilled syringes, a greater amount of syringe configuration information must be input into and accepted by injectors to program and control injection procedures. By providing an injector system having the capability to automatically obtain syringe configuration information from syringes with minimal or no operator intervention, injection procedures can be efficiently programmed and controlled, and/or recorded for billing or other purposes.

SUMMARY OF THE INVENTION

The present invention provides generally apparatuses and methods for sharing information on syringe configuration between syringes and injector systems. The syringe configuration information carried by syringes or other elements can be automatically accessed by or input into injectors to program and/or control injection procedures, such as angiographic, CT, MR and ultrasound injection procedures.

Further, the present invention may be used to generate and maintain data records associated with injection procedures. For example, to update inventory control records and to satisfy medical and insurance billing and cost information requirements, records of information, such as the type of syringe used, the amount of contrast medium used, the type of contrast medium used, the sterilization date, the expiration date, lot codes, the properties of the contrast media, and/or other clinically relevant information, may be generated and maintained for use by, for example, external billing, inventory or control computer systems.

The present invention provides a syringe for use with a powered injector including a drive member and a having a detector or detection circuit in communication therewith. The detector may be incorporated within the injector. The syringe preferably comprises an elongated body and a plunger slidably disposed within the elongated body and operable to be driven by the drive member. The syringe also preferably comprises a means or mechanism adapted to convey syringe information to the detector or detection circuit.

The mechanism adapted to convey syringe information to the detection circuit may be included in an encoded element (for example, a cap that fits over the syringe plunger or a fluid path element that is connected to the syringe) that includes a store of syringe information and is separate from and connectable to the syringe. Alternatively, the attachable element incorporating the syringe information may be connectable or attachable to the injector or the detector.

In general, syringe information can be conveyed using various energy sources including, for example, electrical, magnetic, radio frequency, optical and ultrasound. Physical indicia can also be used. Combinations of one or more energy sources and/or physical indicia are also possible.

In the case that the information is encoded directly upon the syringe, areas of intimate contact between the syringe and another element are preferably used to convey the information. Because intimate contact is made between the plunger and the drive member, for example, the plunger/drive member interface provides a good place to transmit information regarding syringe configuration to the detection circuit. The present invention thus provides a syringe as described above in which the plunger includes information regarding the syringe encoded thereon. This information may be conveyed to the detector of the injector via one or more readout members or sensors in the drive member of the injector.

In the case of a number of syringes, a pressure jacket (typically, a robust cylindrical element) enables a relatively thin-walled syringe to be used at high pressures. In one embodiment of the present invention, information stored on the syringe (preferably, on the elongated body or barrel of the syringe) is communicated from the syringe to the pressure jacket.

Also, heaters are sometimes used to heat the contents of a syringe to, for example, body temperature (see, for example, U.S. Pat. No. 4,006,736). The interface between the syringe and such a heater also provides a useful interface for transfer of information.

In the case the information is encoded directly upon the syringe or upon an encoded element attached to or connected to the syringe, the syringe may comprise alignment elements that cooperate with associated alignment elements upon an injector, a pressure jacket or a heater element to align encoded elements on the syringe with cooperating readout elements of the detector.

According to one aspect of the present invention, a system is provided comprising a syringe for use with a powered injector to inject a fluid into a patient. The syringe includes an elongated body and a plunger slidably disposed therein as described above. The powered injector includes a drive member and is in communication with a detector or a detection circuit. The detector is communicative connection with or comprises at least one electrically conductive readout contact member.

The system further includes at least one electrically conductive code contact member adapted to contact and make an electrical connection with the readout contact member(s). The code contact member or members encode or are in communicative connection with encoded information relevant to the syringe configuration to transmit such encoded information to be read by the detection circuit when the code contact member(s) are in electrical connection with the readout contact member(s).

Preferably, the system comprises a plurality of electrically conductive code contact members. Each of the plurality of code contact members may be positioned to contact and make an electrical connection with only one of a plurality of electrically conductive readout contact members.

In one embodiment, the conductive code contact members are brought to a state of either digital high or digital low upon contact with corresponding readout contact members of the powered injector when the syringe and the powered injector are in operative connection. Preferably, one of the readout contact members is maintained at digital ground and the remainder of the readout contact members are maintained at a non-zero potential. Any code contact member in electrical connection with the digital ground readout contact member is preferably interpreted as being in a state of digital low, while those not in electrical connection with the digital ground readout contact member are interpreted as being in a state of digital high.

A binary encoded signal is thus transmitted to the detection circuit of the powered injector. Assuming one code contact member/readout contact member pair is dedicated to digital ground, there are $2^{n-1}$ possible distinct binary codes that can be represented, where n is the number of code contact member/readout contact member pairs. Preferably, the detection circuit in this embodiment comprises a processing unit such as a microprocessor to read and interpret the binary encoded information. Each unique binary code preferably represents an unique syringe configuration.

In another embodiment, each of the code contact members is preferably in electrical connection with a corresponding electrical impedance element. The resistance, capacitance, inductance, or voltage of each of the elements is preferably readable by the detection circuit to provide information to the detection circuit relevant to the syringe configuration. The detection circuit may comprise, for example, a register and/or a processing unit such as a microprocessor.

In a further embodiment, the system preferably comprises at least two electrically conductive code contact members. Each of the code contact members is in electrical connection with a memory. The memory is encoded with information relevant to the syringe configuration. Upon contact and electrical connection with corresponding readout contact members, the encoded information is transmitted to a processing unit of the detection circuit.

The conductive code contact members may, for example, be positioned on the syringe to form an electrical connection with corresponding readout contact members positioned upon, for example, the injector, a pressure jacket or a heating element as described above.

In another embodiment, the system comprises an encoded element that includes at least one electrically conductive code contact member adapted to contact and make an electrical connection with the readout contact member(s). The encoded element may, for example, be incorporated in or attached to a fluid path element that is in fluid connection with the syringe, a cap attachable to the syringe (for example, on the plunger thereof) or a cap attachable to the readout element (for example, on the drive member of the injector). Such an encoded element may provide the syringe information for several successive syringes. One attachment element or cap can, for example, be provided with each box of syringes (for example, a box of 50 syringes). When a new box is opened, a new attachment element or cap with the properly encoded information is installed. Physical mating structures can be provided so that only specific syringes can fit with specific attachment elements. This embodiment can also facilitate use of different manufacturer's syringes with various injectors. If the cap is to be mounted on the drive member, the cap may be domed so that there is no contact with the readout contact members until a syringe is engaged and pushes the cap into contact with the readout contact members. The advantage of this embodiment will be discussed below.

The conductive code contact members of the present invention are preferably shaped to substantially ensure electrical connection with the readout contact members upon operative connection of the syringe to the powered injector. In one embodiment, the conductive code contact members comprise conductive rings extending around the circumference of the body or barrel of the syringe. The code contact members may also comprise concentric conductive rings formed on a rear surface of the plunger to communicate with readout contact members positioned upon a forward surface of a drive member of the injector.

The present invention also provides an encoded element for use with a syringe and a powered injector. The injector includes or is in communication with a detector or detection circuit. The encoded element preferably comprises (i) an attachment mechanism to connect the encoded element to one of the syringe, the injector or the detector and (ii) a store of encoded syringe information readable by the detector. In one embodiment, the attachment mechanism of the encoded element is adapted to detachably connect the attachment element to one of the syringe, the injector or the detector.

The present invention also provides a syringe for use with a powered injector. The syringe comprises at least one code contact member as described above. The powered injector preferably includes a drive member, at least one electrically conductive readout contact member and is in communicative connection with a detector or a detection circuit in electrical connection with the readout contact members.

In the above embodiments, the present invention provides encoding of information that improves reliability of code recognition while maintaining low complexity and low cost relative to other syringe components. When electrical connection is made between the plunger and the drive member, the present invention has the added benefit of allowing the injector to sense when the plunger and drive member have made contact. In the case of pre-filled syringes in which the plunger can be located anywhere along the barrel, this "automatic docking detection" feature simplifies the act of connecting and then stopping the motion of the injector drive member and the syringe plunger without operator intervention.

According to another aspect of the present invention, a syringe for use with a powered injector includes an elongated body, a plunger slidably disposed within the elongated body, and an electronic storage system adapted to convey information relevant to the configuration of the syringe to a detection circuit of the powered injector without connective contact between the electronic storage medium and the detection circuit.

In this aspect of the present invention, energy is transmitted between the electronic storage system and the detection circuit without connective electrical contact therebetween. This energy provides the information relevant to the configuration of the syringe to the detection circuit. Preferably, the information is transmitted from the electronic storage system to the detection circuit via a radio frequency (RF) signal. The electronic storage system preferably includes a transponder in communicative connection with a memory. The detection circuit preferably comprises a transmitter and a receiver. The transmitter transmits an RF signal to the transponder which responds by transmitting an RF signal to the receiver. The RF signal transmitted by the transponder contains the information relevant to the configuration of the syringe. Frequencies above and expecially below the RF range may be used if the geometry and information transfer rate permit it.

The present invention, along with further aspects and attendant advantages, will best be understood by reference to the following detailed description taken in conjunction with the accompanying drawings.

BRIEF DESCRIPTION OF THE DRAWINGS

FIG. 4A illustrates an embodiment of a printed circuit board comprising contact pins.

DETAILED DESCRIPTION OF THE INVENTION

Figure 1A:
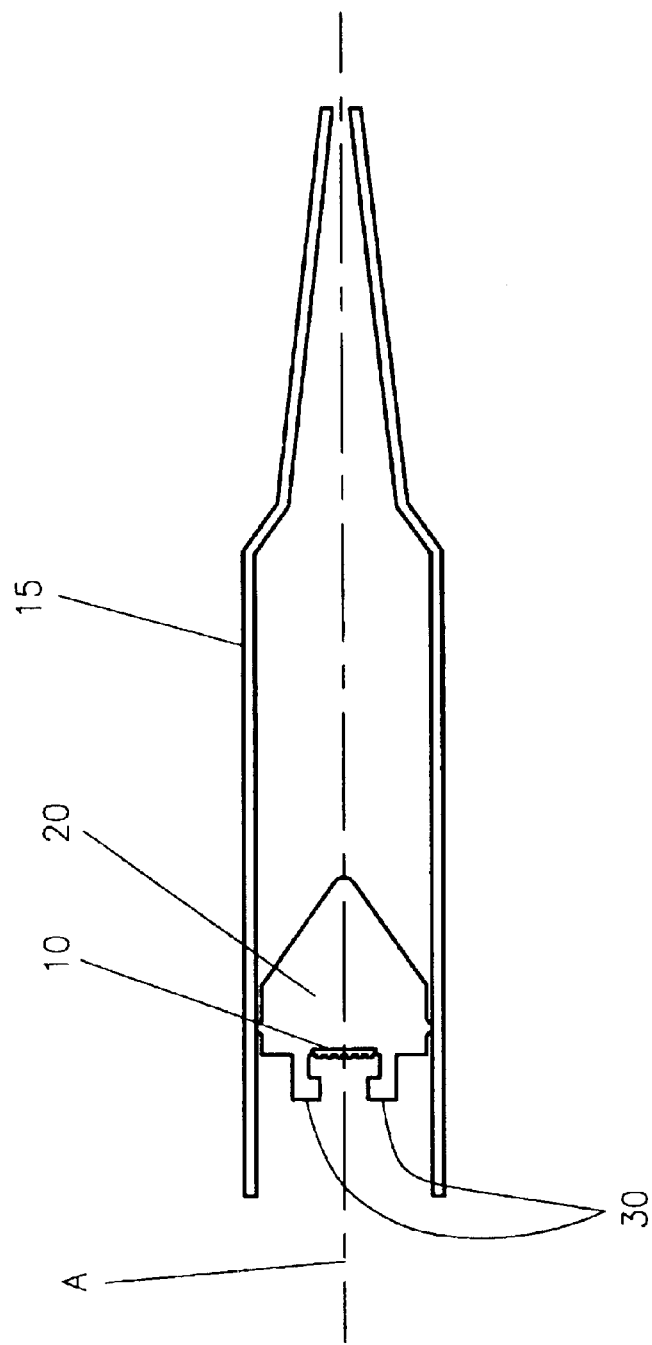
FIG. 1A illustrates a side cross-sectional view of a plunger of the present invention slidably disposed within a syringe.
Figure 1B:
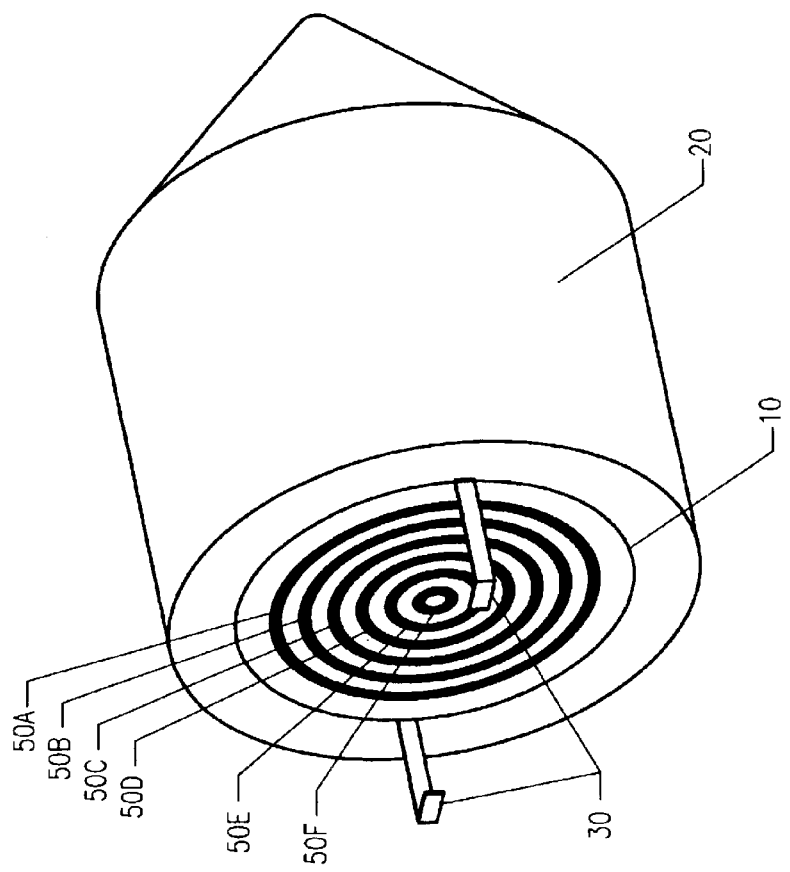
FIG. 1B illustrates a rear perspective view of the plunger of FIG. 1A.
Figure 1C:
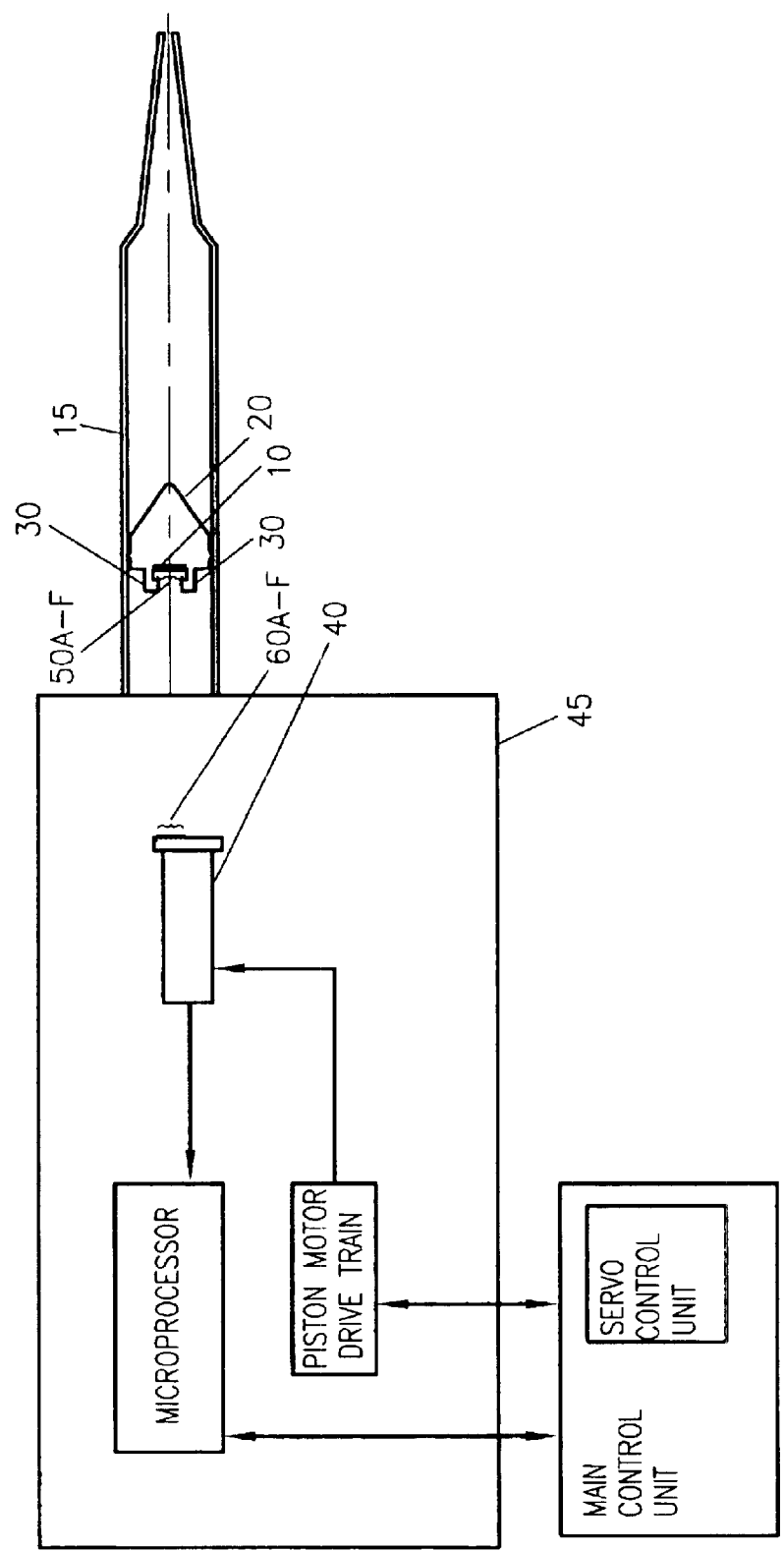
FIG. 1C illustrates a side cross-sectional view of an injector system comprising the syringe and plunger of FIG. 1A.

In the embodiment illustrated in FIGS. 1A and 1B, encoded information in the form of a printed circuit board (PCB) 10 is mounted, for example, in a slot at the rear of a syringe plunger 20. Plunger 20 is suitable to be slidably disposed within the barrel of a syringe 15 to pressurize injection fluid contained within syringe 15. Plunger 20 preferably comprises an attachment mechanism such as capture members 30 for forming a releasable connection with a powered drive member such as a drive piston 40 of a powered injector 45 shown in FIG. 1C. Examples of syringes and injector configurations generally suitable for use in the present invention are disclosed in U.S. Pat. Nos. 4,006,736, 4,677,980, 5,300,031 and 5,383,858 and U.S. patent application Ser. No. 09/033,264, filed Mar. 2, 1998, and entitled "Syringes and Plungers for Use Therein," the disclosures of which are incorporated herein by reference.

As used herein to describe syringe 15 and plunger 20, the terms "axial" or "axially" refer generally to an axis A around which syringe 15 and plunger 20 are preferably formed (although not necessarily symmetrically therearound). The terms "proximal" or "rearward" refer generally to an axial direction toward capture members 30. The terms "distal" or "forward" refer generally to an axial direction toward the end of plunger 20 opposite capture members 30. The term "radial" refers generally to a direction normal to axis A.

Figure 3A:
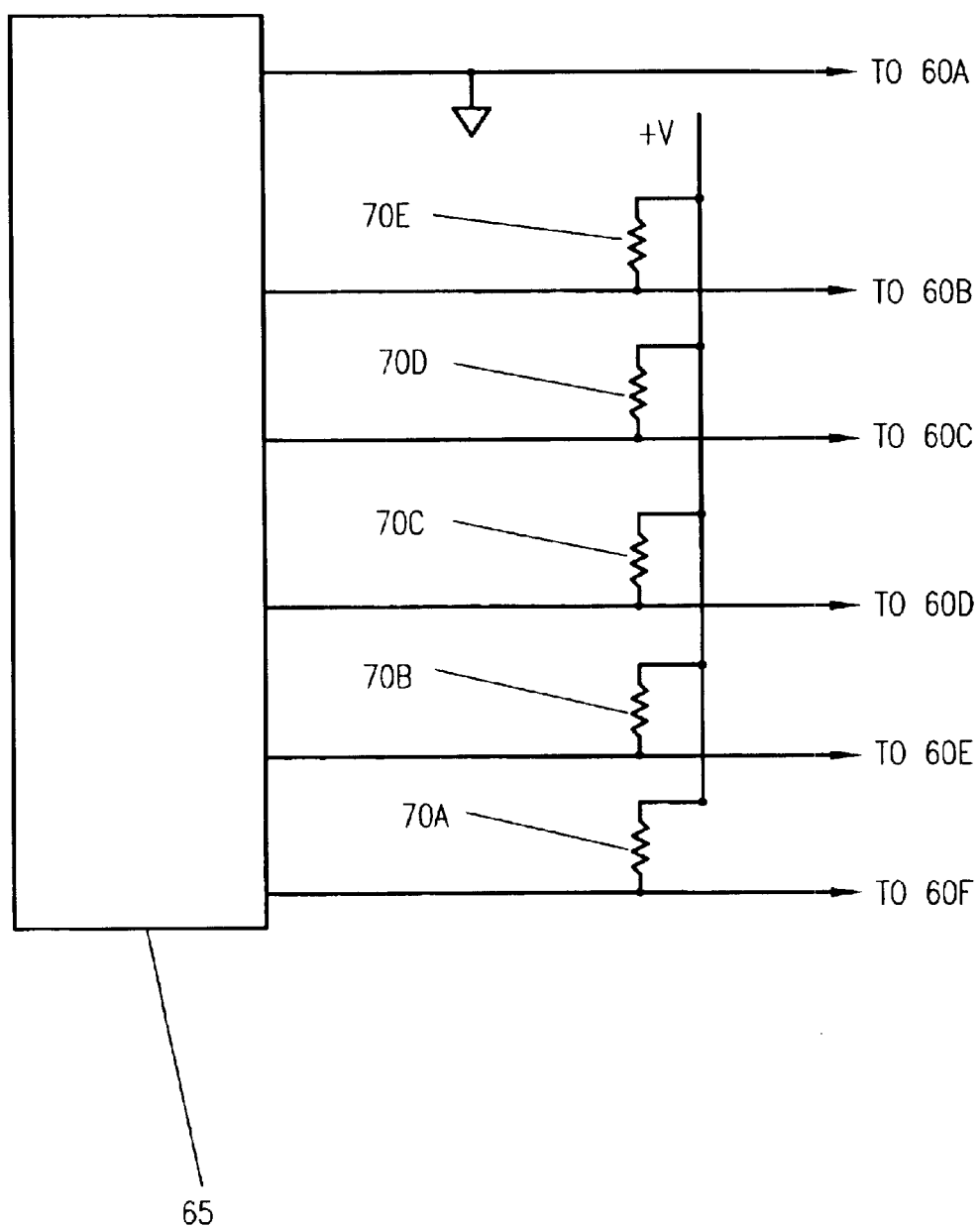
FIG. 3A illustrates a diagram of the electrical circuit of the connective pins of the drive member.

Printed circuit board 10 preferably comprises a number of plunger contact members preferably formed as concentric rings 50 (see, for example, FIG. 1B) comprising rearward facing conductive surfaces. In one embodiment, best illustrated in FIGS. 3A and 3B, printed circuit board 10 comprises six concentric rings 50A through 50F. The conductive surface of rings 50A through 50F face rearward to be contacted by a corresponding set of electrically conductive readout contact members or pins 60A through 60F preferably positioned at a forward end of the injector drive piston 40. Pins 60A through 60F are preferably positioned radially on the front end of drive piston 40 such that pin 60A contacts ring 50A, pin 60B contacts ring 50B, pin 60C contacts ring 50C, pin 60D contacts ring 50D, pin 60E contacts ring 50E and pin 60F contacts ring 50F when drive piston 40 forms a connection with plunger 20.

In one embodiment, one of pins 60A through 60F, for example, pin 60A, is electrically connected to ground. All pins with the exception of grounded pin 60A, are electrically connected to a known voltage, such as +5 volts, (see FIG. 3A), for example, on another printed circuit board preferably located within the injector. The voltage on each pin on drive piston 40 can be interpreted electronically as a single bit in a binary code. The binary code uniquely identifies the syringe configuration or characteristics. Preferably, if the code is not present or is improperly read, the injector will not function.

Figure 3B:
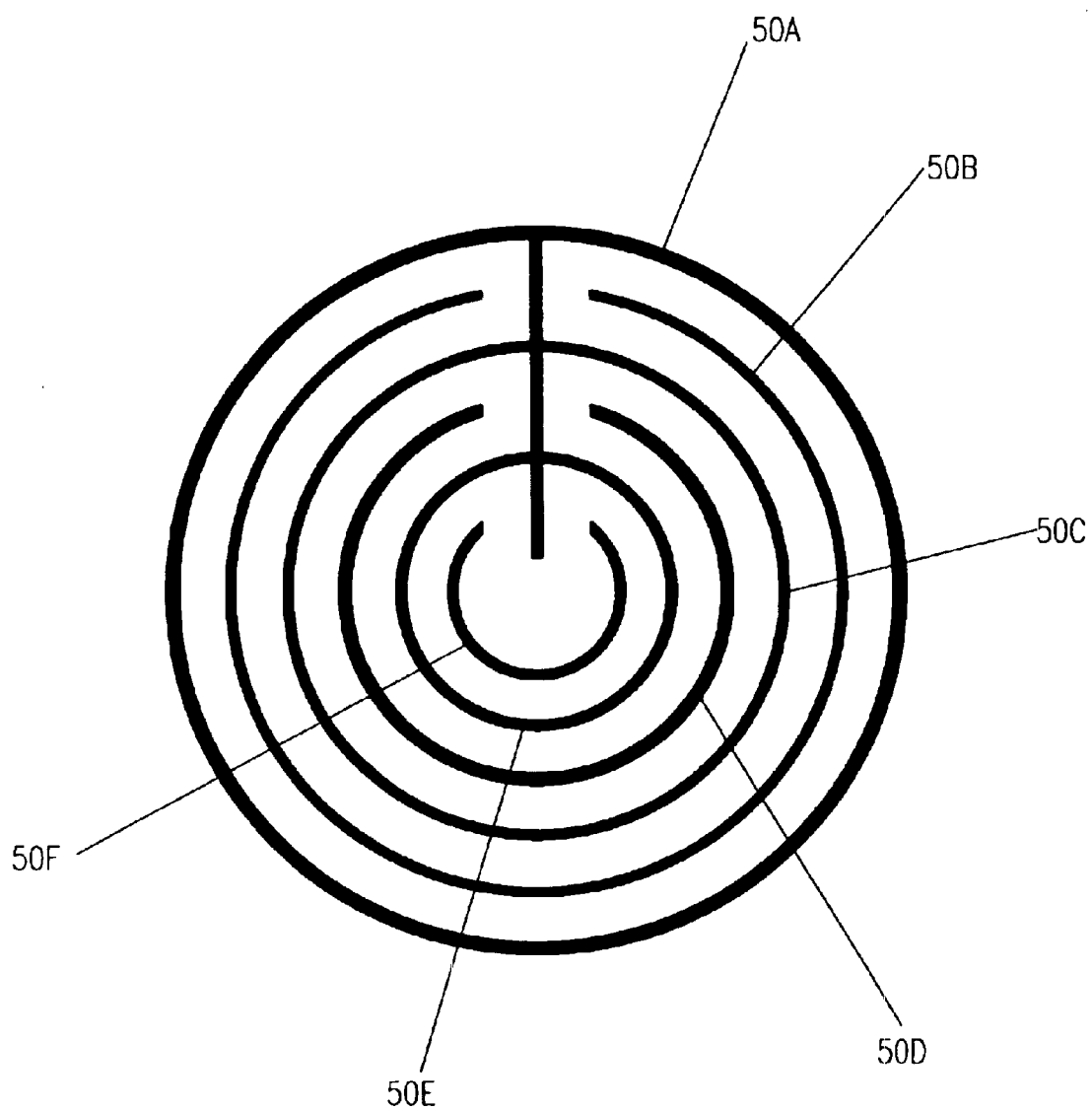
FIG. 3B illustrates a diagram of one embodiment of electrical connection between the rings of the plunger.

An example of a coded plunger printed circuit board is shown in FIG. 3B. Preferably, one of the concentric rings (for example 50A) is connected to electrical ground through corresponding pin 60A on the end of the drive piston 40 when contact is made. Other concentric rings may be electrically connected to or isolated from the ground ring 50A. When read out by the circuit of FIG. 3A, those rings that are connected to 50A will be read out as a logical 0 and those that are not connected will be a logical 1. To avoid the possibility that a readout element will touch the radial conductor, it can be covered with an insulating layer such as solder mask, or a two sided printed circuit board may be used with the concentric rings choosably connected to 50A by printed wiring on the underside of the printed circuit board through holes or vias.

Those concentric rings not electrically connected to ground ring 50A are allowed to "float" being in an electrical high-impedance state. The voltage measured on each of pins 60B through 60F after contact with rings 50A through 50F can be interpreted electronically as a single bit in a binary code. The binary code preferably uniquely identifies the syringe characteristics. In the embodiment of FIG. 3B, a connection to digital ground equals a digital low state (0), while no connection to digital ground equals a digital high state (1). The code of plunger printed circuit 10 is thus 10101.

Printed circuit board 10 on plunger 20 thereby acts as a code to identify syringe 15 and its contents. Assuming one pin/ring pair is dedicated to digital ground, there are $2^{n-1}$ possible binary codes that can be represented, where n is the number of pin/ring pairs. For example, if there are 8 concentric rings and one is allocated for digital ground, there are $2^7$ or 128 possible binary codes that can be represented.

As with any kind of switch, a debounce circuit (not shown) is preferably provided to read an electrically stable code. The debounce circuit can comprise hardware or, if a microprocessor is used to read the state of the contact switches (that is, pin/ring pairs), it can comprise software.

In a simple operational mode shown in FIG. 3B, before contact is made between piston 40 and plunger 20, the state of each piston pin is held in a logic high state by pull up resistors 70A to 70E, with the exception of a single common pin 60A which is held at ground. When one or more of the pin signals starts to change to logic low as contact is made, a signal is preferably provided to the injector detection circuit indicating that piston 20 and plunger 40 are in proximity. After a suitable time interval when the electrical readings on all pins are stable, the potential of those pins which are touching a code element electrically connected to the common pin 60A will be at the potential of the common pin 60A, ground in this example. An electronic control device 65, for example a microprocessor, can interpret the resultant binary code and can then allow the injector system to alter its operation for the specific syringe configuration.

Printed circuit board 10 comprises concentric ring contact members 50A through 50F so that the printed circuit board 10 can be disposed within syringe 10 in any rotational orientation about axis A, thereby simplifying the manufacturing process. As clear to one skilled in the art, however, many other contact configurations are possible. Several other contact configurations are discussed below.

Printed circuit board 10 can, for example, be mechanically fit into an appropriate receptacle or slot in the rear of plunger 20, or it can be insert molded. Because prefilled syringes can be subjected to high temperatures and pressures during sterilization, a printed circuit board installed prior to autoclave sterilization must be capable of surviving autoclave sterilization conditions. In a preferred embodiment, printed circuit board 10 is fabricated from Kapton®, a high temperature polyamide with a low coefficient of thermal expansion. Etched circuits on Kapton® will not burn, deform, or crack during a standard steam autoclave cycle which ramps up to approximately 121° C. at approximately 16 psi for approximately 3 hours.

Alternatively, a printed circuit board or another carrier of electrical conducting contact members can be placed on plunger 20 or elsewhere after autoclave sterilization. Indeed, existing syringe plungers are easily retrofitted to practice the present invention. In that regard, a printed circuit board or another carrier of electrical conducting contact members, can be part of a "cap" that is fitted, for example, to the rearward surface of an existing plunger design. Depending upon the economics and ease of use, the cap may be preassembled with one cap per each plunger or there may be one cap for a number of plungers to reduce the cost associated with disposing of each cap when a syringe and its plunger are discarded.

Figure 4B:
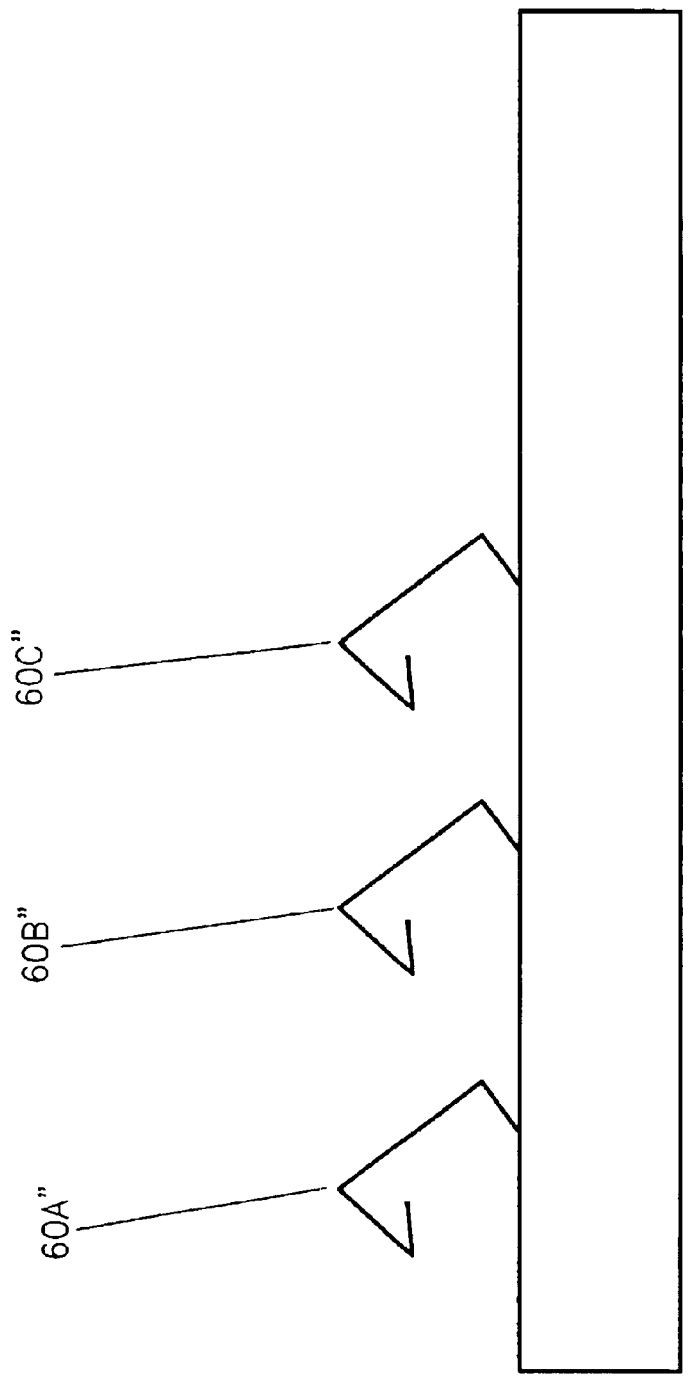
FIG. 4B illustrates another embodiment of a printed circuit board comprising contact pins.

Pins 60A through 60F are preferably gold-coated, rounded pins that are capable of digging into the corresponding conductive rings on plunger printed circuit board 10. Preferably, pins 60A through 60F are biased forward. As illustrated in FIG. 4A, pins 60A', 60B' and 60C' can be mounted in an elastomeric matrix 70 to provide such a forward bias. The forward bias of pins 60A' through 60C' allows pins 60A' through 60C' to ride along the corresponding conductive rings while substantially ensuring proper contact. The forward bias thus substantially compensates for any surface irregularities in the conductive rings of the plunger printed circuit board. In an alternative embodiment illustrated in FIG. 4B, forward-biased pins 60A" through 60C" comprise cantilevered leaf springs or wipers that ride along the corresponding conductive rings. The pins preferably slide along the printed circuit board contacts because, at the end of an injection, syringe 15 can be removed from the injector head by, for example, rotating the syringe barrel to release plunger 10 from drive piston 40. This rotating action must not damage the electrical contacts on drive piston 40. Moreover, the wiping action of the pins against the corresponding conductive rings cleans the pin surface of any dirt or contrast media that might impede electrical contact.

Figure 2A:
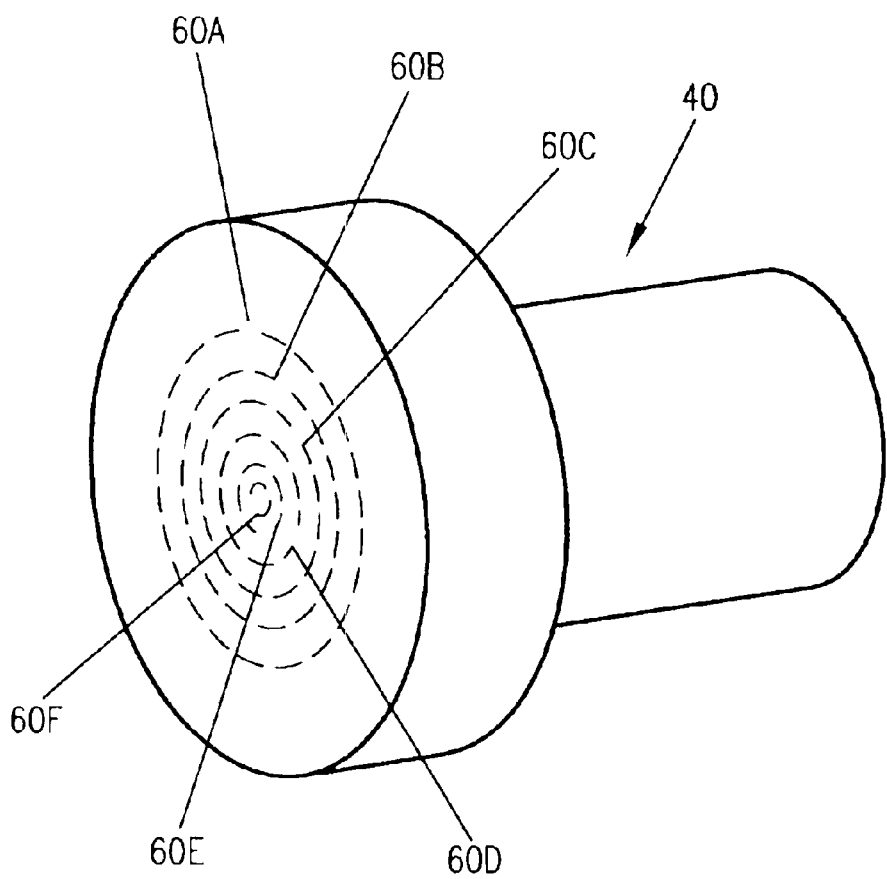
FIG. 2A illustrates a front perspective view of a drive member comprising several conductive contact pins.
Figure 2B:
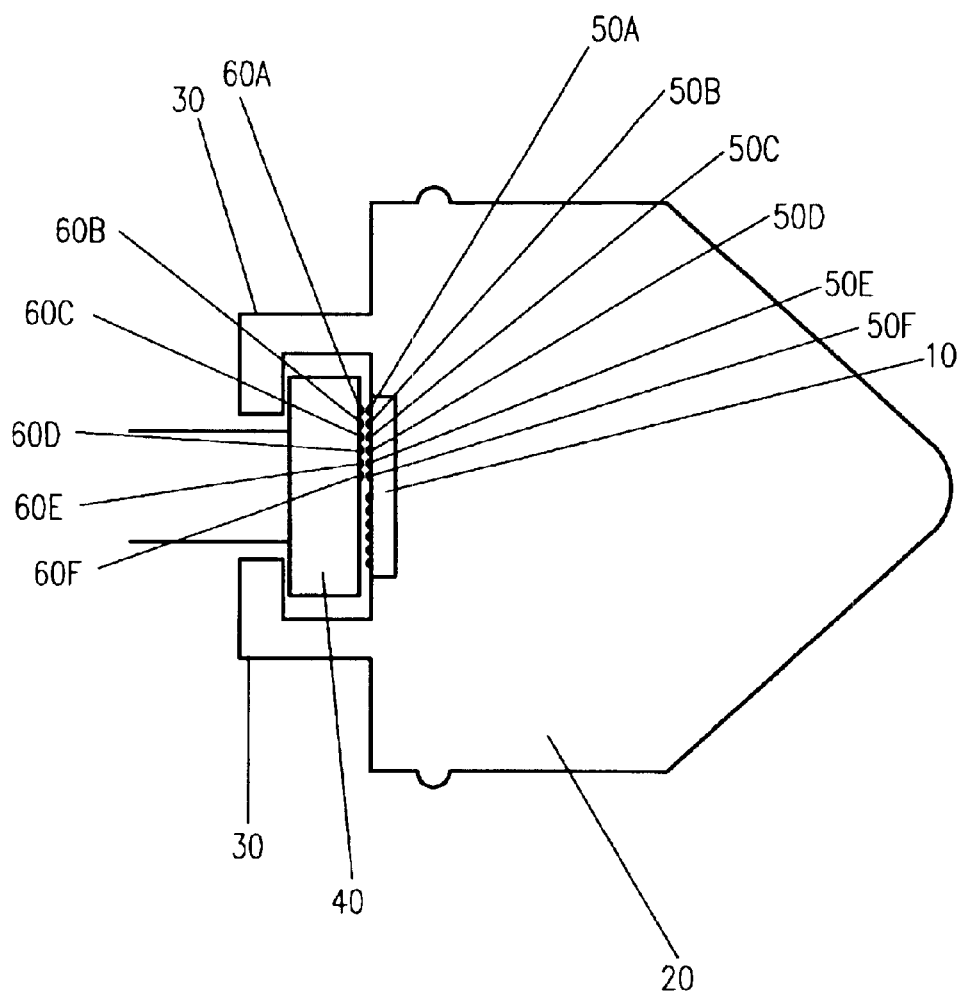
FIG. 2B illustrates a side cross-sectional view of a plunger of the present invention in contact with a drive member.

Although pins 60A through 60F are preferably positioned radially about axis A to substantially ensure contact with corresponding rings 50A through 50F, respectively, the angle at which they are positioned about axis A is not important. As illustrated in FIGS. 2A and 2B, respectively, the pins can, for example, be oriented in a spiral configuration or in a straight line along the forward face of drive piston 40. Pins 60A through 60F are preferably electrically connected to a wire harness or flex circuit (not shown) that is connected to a detection circuit (not shown) in the injector head or otherwise in communication with the injector controls.

There may be multiple pins, not shown, at a specific radius to provide some redundancy to the contacts. These pins may simply be connected to the same wire in the wiring harness or they may each be separately connected to the detection circuit so that the detection circuit can determine if a pin is no longer functioning and alert the operator or the service provider that a pin is broken or needs to be cleaned, before it prevents the code from being read.

Another error checking method involves use of one of the data bits as a parity bit. A parity check uses only one additional bit. If a number of redundant bits are available, Hamming codes or other error detection or correction codes known to those skilled in the art may be used.

The above embodiments use a printed circuit board as the carrier for the conductive element. However, there are many other ways conductive elements can be incorporated. For example, a solid conductive sheet can be used with insulating surfaces selectively placed in rings to prevent contact. This embodiment avoids the gaps seen in FIG. 3B. It also has the advantage that the metal and insulator can be much more robust with respect to temperature during sterilization. An inexpensive metal, such as copper coated steel, can be used. The Insulating surfaces can, for example, be TEFLON® or KAPTON® bonded to the metal, or any type of high temperature, moisture resistant paint.

In an alternative embodiment, formed metal rings can be insert molded into the plunger. The pattern of connections can be made before insert molding or can include tabs that are broken off later to create the specific code. The conductive pattern of FIG. 3B can be hot stamped onto the plunger using conductive metal films or printed using conductive ink. Alternatively, a contiguous conductive layer can be hot stamped or printed onto the plunger. Subsequently, selected segments are removed by mechanical means or laser trimming to create the desired pattern. Alternatively, the rings can all be connected to the common code element by fusible elements. These fusible elements can be opened or closed by appropriately pulsing them with energy.

Figure 5A:
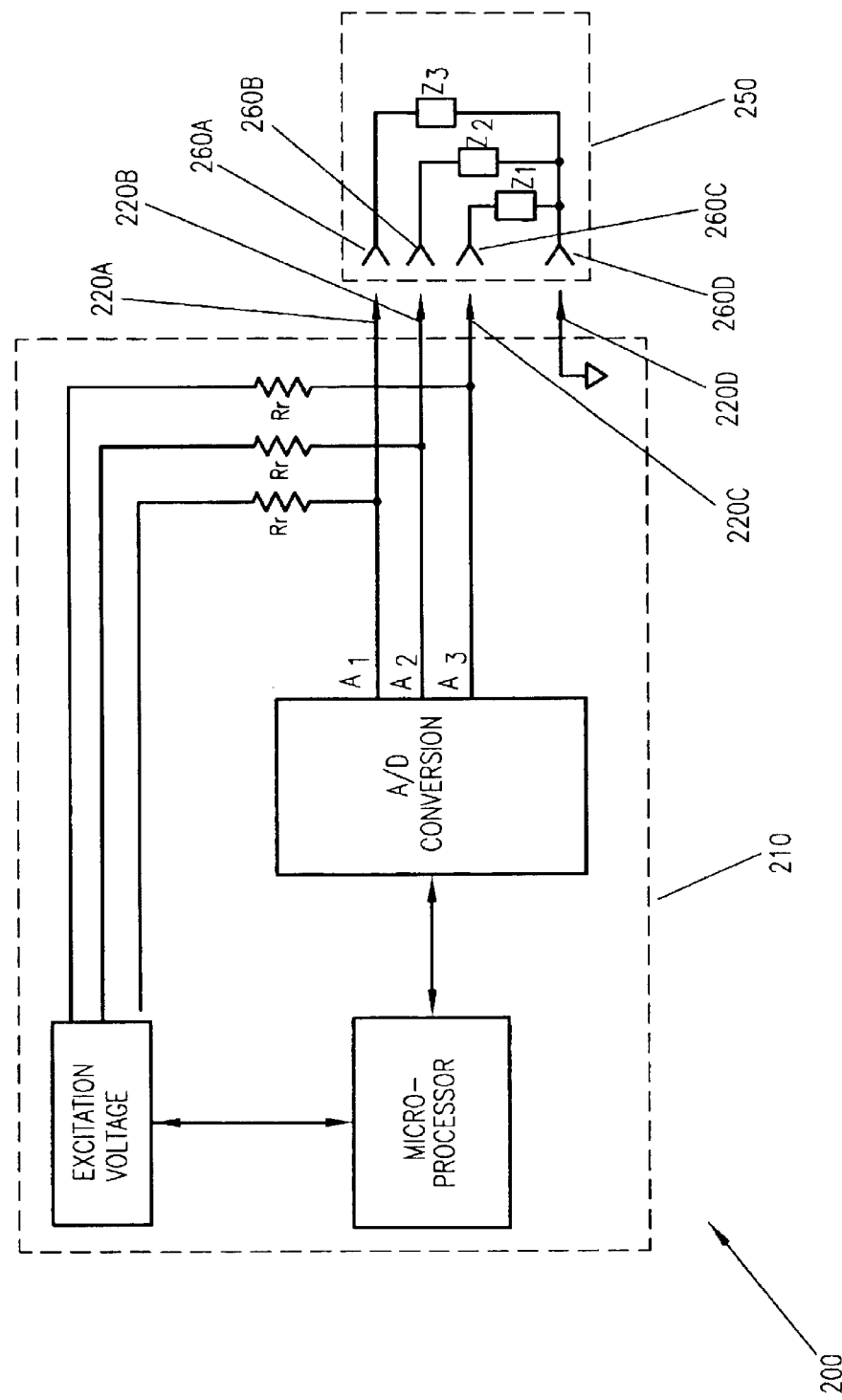
FIG. 5A illustrates an electrical schematic view of a system using impedance elements to encode information relevant to syringe configuration.
Figure 5B:
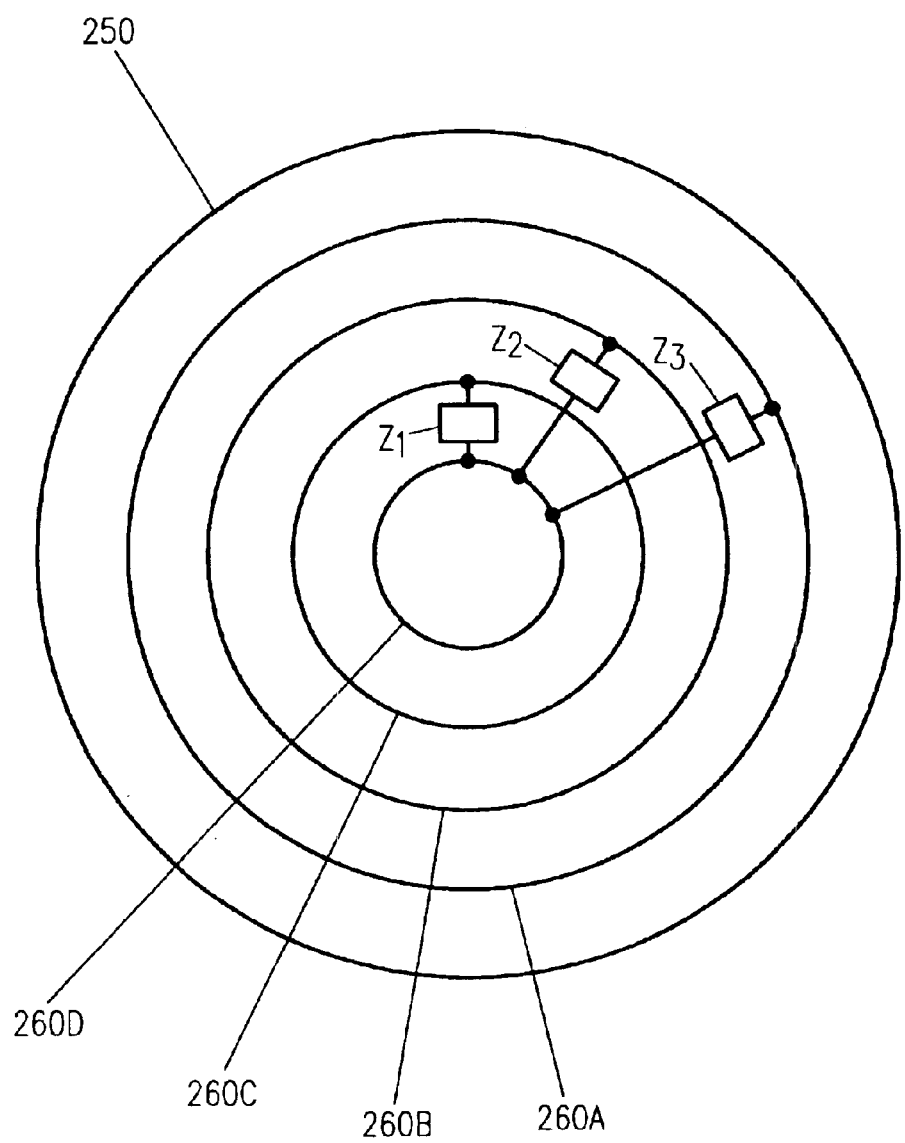
FIG. 5B illustrates an embodiment of a plunger printed circuit board for use in the injector system of FIG. 5A.

Another embodiment of the present invention is illustrated in FIGS. 5A and 5B. In this embodiment, an injector system 200 comprises a powered injector 210 and a syringe (not shown) as described above. The syringe comprises a plunger (not shown) including a printed circuit board 250, preferably on the rear surface of the plunger. Printed circuit board 250 is modified from that described above to extend the range of coded information beyond that available using binary coding.

In that regard, one or more circuit elements, for example, $Z_1$, $Z_2$ and $Z_3$, are preferably connected on one side with a common contact member 260D and on the other side with a corresponding, separate contact member 260C, 260B and 260A, respectively. The impedance elements can be resistors, capacitors, inductors, resonant circuits, zener diodes, or more complicated circuits. Impedance refers to the current versus voltage relationship for the element. It may be a function of frequency for some elements. Resistors are the simplest impedance elements. For instance resistors $Z_1$, $Z_2$ and $Z_3$ are set up as legs of resistor dividers. The voltage measured (designated $A_1$, $A_2$, and $A_3$ in FIG. 5A) at the junction of each of resistor $Z_1$, $Z_2$ and $Z_3$ with a reference resistor $R_r$ (preferably located in powered injector 210) represents information about the configuration of the syringe. Voltages $A_1$, $A_2$, and $A_3$ are preferably transmitted to a detection circuit comprising an analog-to-digital (A/D) converter. The A/D converter is preferably in communicative connection with a processing unit such as a microprocessor.

The resolution of the measurement of voltages $A_1$, $A_2$, and $A_3$ (which is limited by noise and the resolution of the A/D) converter) determines the number of unique states that can be encoded. For example, if the resolution of each analog voltage measurement of the circuits comprising the contact members is ten levels, and there are three contact members, 1000 possible states can be encoded. The precision of the value of the impedance element can also limit the number of discernable levels.

Zener diode impedance elements operate in a similar fashion. A zener diode has a fixed reverse bias voltage over a broad range of currents. Thus the voltages at $A_1$, $A_2$, and $A_3$ are controlled by the characteristic or breakdown voltages of the zener diodes at $Z_1$, $Z_2$, and $Z_3$.

To sense information coded in inductive, capacitive, and resonant impedance elements, the excitation voltage preferably varies over time. Such variation can be in the form of a pulse, a square wave, or a sine wave of a specific frequency. The measurement of the voltages $A_1$, $A_2$, and $A_3$ is coordinated with the state of the excitation voltage to give a measure of the capacitance or inductance of $Z_1$, $Z_2$, and $Z_3$. If resonant circuits are used, the excitation voltage is preferably a sine wave and the frequency is varied. Depending on the specifics of the resonant circuit used, the voltage at $A_1$, $A_2$, and $A_3$ as a function of frequency provides the coded information. In the case of resonances, one Z element can be made from several inductors and capacitors and can have multiple resonances, so the information storage is even more dense than simple conductive, resistive, capacitive, inductive or zeners. Given the sophistication of integrated circuits, a circuit with a complicated impedance function can readily be built that makes the readout voltage $A_1$ go up and down as the excitation voltage is changed. At some point, the sophistication of this integrated circuit approaches that of the digital memory discussed below, and the memory becomes the preferable storage device.

Applying the concept of varying the excitation voltage allows the elimination of the common contact, if that is of benefit. The common contact can be replaced by capacitive coupling to a reference or ground. There need not be a conductive common contact. There can also be multiple excitation voltages, up to the maximum of a different excitation voltage for each impedance element.

Figure 5C:
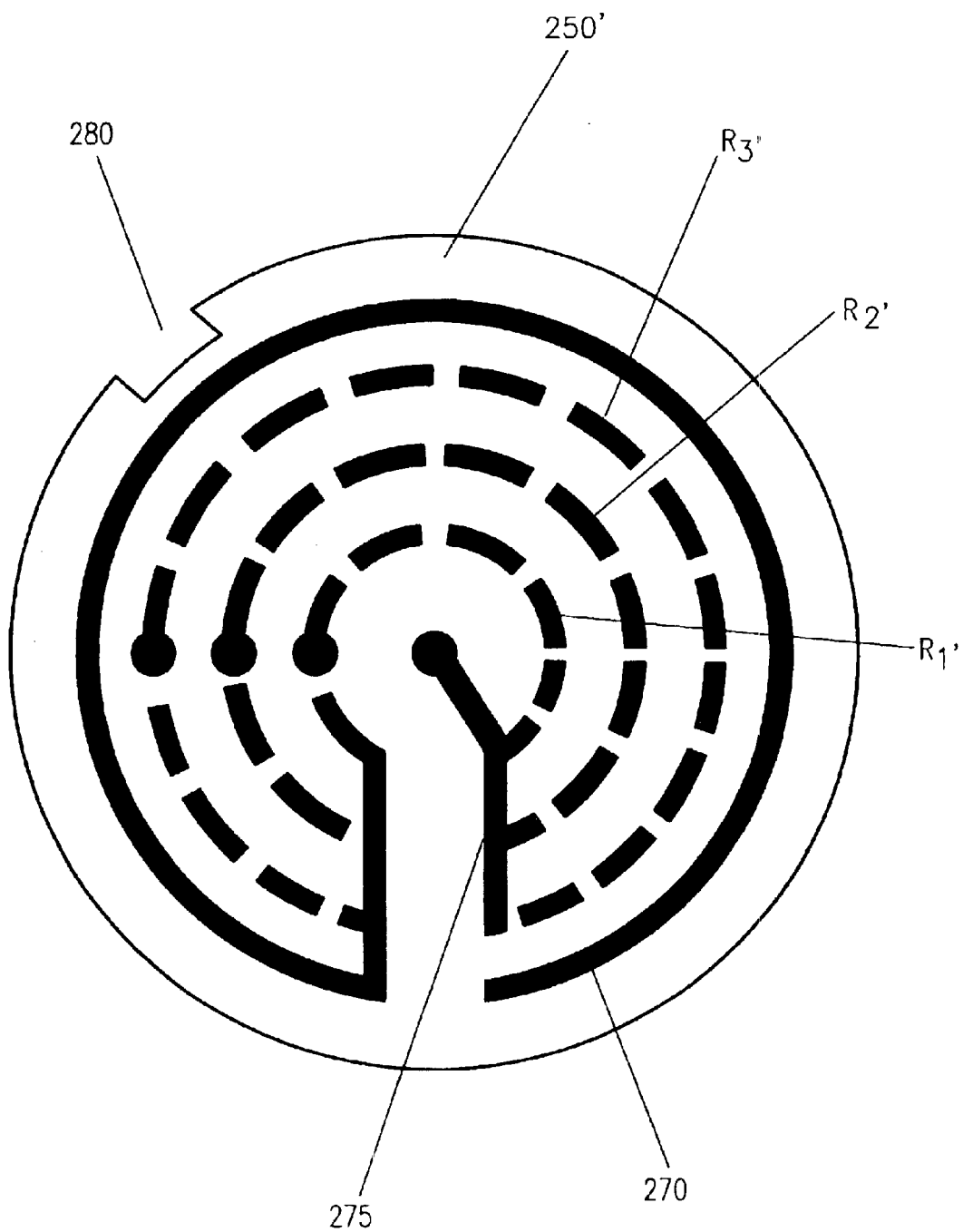
FIG. 5C illustrates another embodiment of a plunger printed circuit board for use in the injector system of FIG. 5A including surface printed resistors.

FIG. 5C illustrates another embodiment of the present invention in which the discrete resistors or other impedance elements of FIG. 5B are replaced by printed resistive contact members or contact elements $R_1'$, $R_2'$ and $R_3'$. In this embodiment, because the voltage at the point of contact is sensitive to the location thereof along the concentric resistive contact elements $R_1'$, $R_2'$ and $R_3'$, printed circuit board 250' is preferably oriented in a known manner. In that regard, a key slot 280 is preferably provided in printed circuit board 250' to ensure proper alignment of printed circuit board 250' in relation to the plunger. As will be described later, an alignment path is needed between the code element and the readout elements to ensure accurate readout.

By way of example, the contact points are illustrated as circles along the length of resistive contact elements $R_1'$, $R_2'$ and $R_3'$ in FIG. 5C. With an excitation voltage applied to element 275 and element 270 connected to ground, the voltage at the code element contact point is a function of the ratio of resistance from the code element contact point to element 270 divided by the total resistance from 275 to 270. The resistor ratio can be changed by printing with different resistivity inks or varying the width of the resistive segment. It is also possible to use conductive ink for part of the segment to further reduce the resistance of that segment. Laser, physical, or other trimming after manufacture can also be used to change the resistance values. The readout circuit does not need to include resistors $R_r$ because the resistors from the contact point to the excitation voltage are included on the printed circuit board.

To avoid the need to have an alignment path, a double sided circuit board can be employed. On the side opposite the printed resistors, circular concentric rings are placed. The contact points shown in 5C then represent feed through to the separate concentric rings. A second alternative to avoid the need for an alignment path is to reverse the points and rings as described above. If the contact points incorporate spring contacts similar to those of FIG. 4B and the readout elements on the drive element are concentric rings, rotational alignment is not necessary.

Additionally, other manufacturing methods may be used to create the assembly of impedances described above. Among these methods are attaching the impedance elements to a lead frame, covering them with a protective material such as an epoxy, insert molding them into the plunger, and then breaking off the attachment bar of the lead frame to provide separate impedances. This technique is similar to the manufacture of SIP resistor packages known to those skilled in the art.

In general, the conductive coding methods described earlier are a specific case of impedances, where the impedance values $Z_1$, $Z_2$, and $Z_3$ are limited to values much less than $R_r$ and much greater than $R_r$. This simplifies the circuit because logic levels replace the A/D converter, at the price of conveying only one bit of information for each impedance element.

Figure 6:
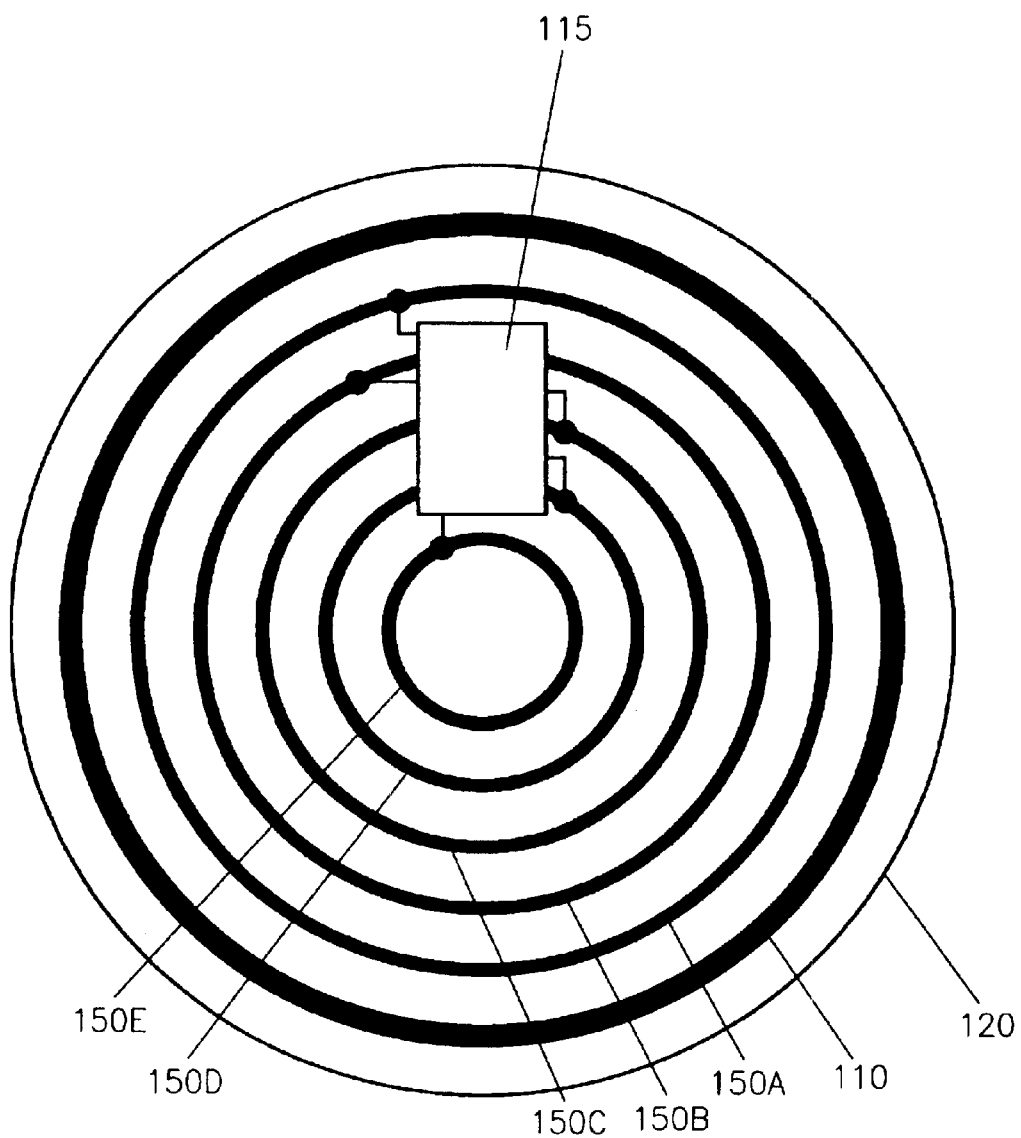
FIG. 6 illustrates a rear view of a plunger of the present invention comprising a printed circuit card with a memory for storing information relevant to an injection procedure.

Another embodiment of the present invention is illustrated in FIG. 6. In the embodiment of FIG. 6, a printed circuit board 110 is mounted on or attached to the rearward end of a plunger (not shown) as described above. As also generally described above, a corresponding set of electrical contacts (not shown) is provided on the forward end of the drive piston (not shown). In the embodiment of FIG. 6, the passive printed circuit boards or cards of the embodiment of FIGS. 1A through 5C are replaced by a printed circuit board 110 with an active memory 115. Memory 115 can, for example, comprise a ROM, EPROM or EEPROM which can be surface-mounted on printed circuit board 110 with, for example, five electrical contacts 150A through 150E positioned upon a rear surface of plunger 120 to be contacted by contact pins (not shown) on a forward surface of the drive piston. Printed circuit board contacts 150A through 150E preferably comprise concentric rings as described above. Contacts 150A through 150E may, for example, comprise +5 volts, ground, data in, data out, and clock. The EPROM or EEPROM may be programmed either before or after construction of printed circuit board 110. (A ROM is programmed when manufactured.) The EPROM can also be programmed immediately before insertion in the plunger. Elaborate codes with hundreds of code bits (and redundant check bits) can be programmed into memory 115 to uniquely identify syringe configuration/characteristics determined during production.

Moreover, recent innovations such as the DS1991 Touch Memory Button™ available from Dallas Semiconductor, allow an EPROM to be read on contact with only two electrodes (ground and data), and also provide for built-in code error checking. Power and clock are derived from the serial data line.

Upon contact between plunger 120 and the piston (not shown), power is applied to memory 115 and the stored code is read out. The code is preferably interpreted by a processor in the injector to accordingly modify operation of the system. Modifications in operation pertain to, for example, volume delivered, fluid pressure measurement, flow rate, limits of piston travel, and limits of pressure as described above. All of the latter parameters are affected by syringe parameters that can be encoded in memory 115.

Memory 115 can also comprise a non-volatile memory component that can be programmed by the injector to record parameters of the completed injection. Such a system can also record whether or not the syringe had been used previously in order to prevent subsequent reuse.

It should be noted that the circular elements mating with pins described above require axial alignment but not rotational alignment. The degree of axial alignment commonly provided by the syringe mounting means is sufficient. The same robustness to rotational misalignment can be achieved if the pins are on the plunger and the rings are on the drive member. The pins can simply be broken off slightly below the surface to prevent contact and encode information. This would also make it easier to incorporate impedance or conductive elements in the plunger by insert molding. The structure can, for example, be very similar to a SIP circuit package.

Figure 7A:
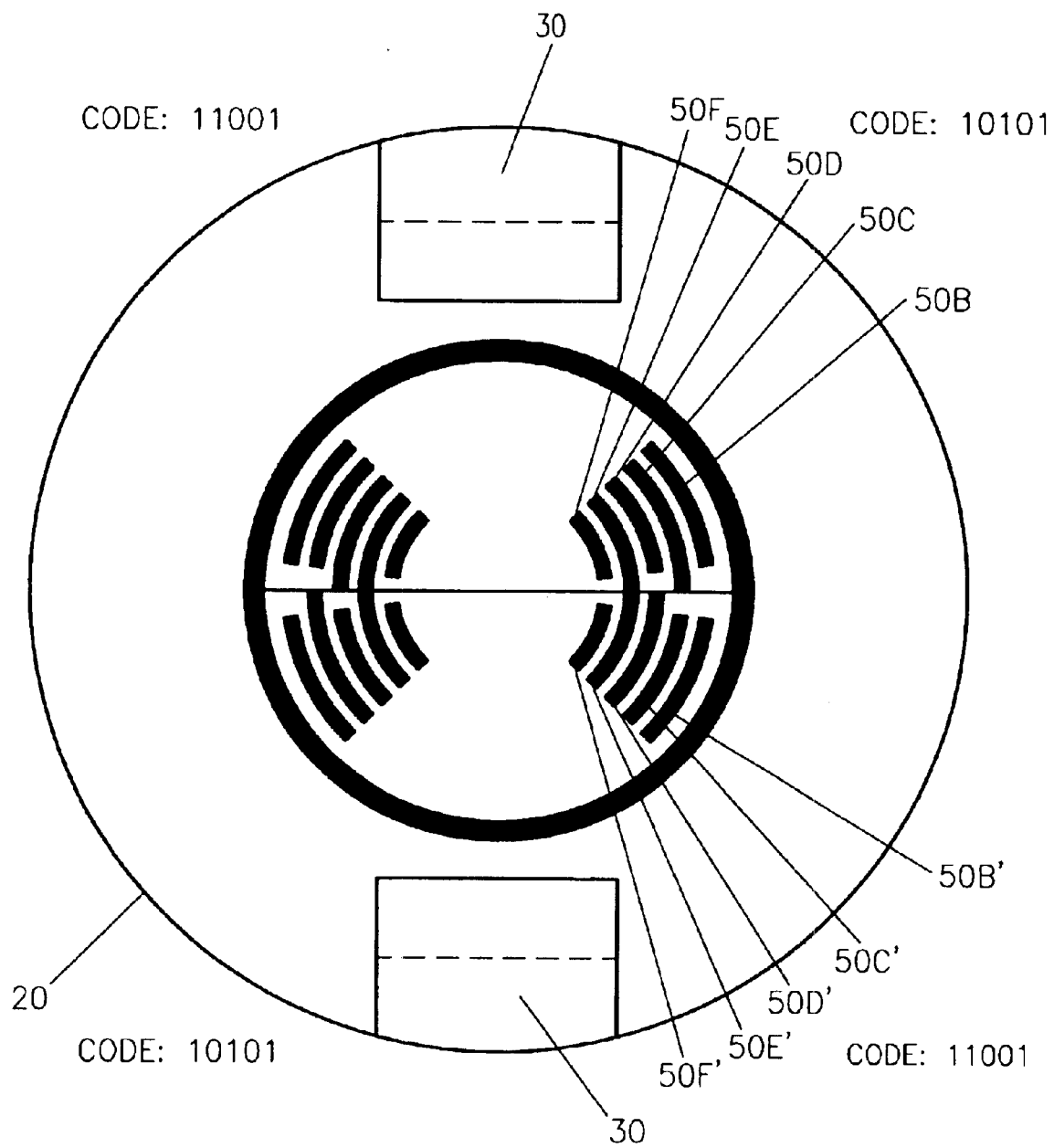
FIGS. 7A and 7B illustrate examples of information encoded for two-dimensional alignment with associated readout contacts.
Figure 7B:
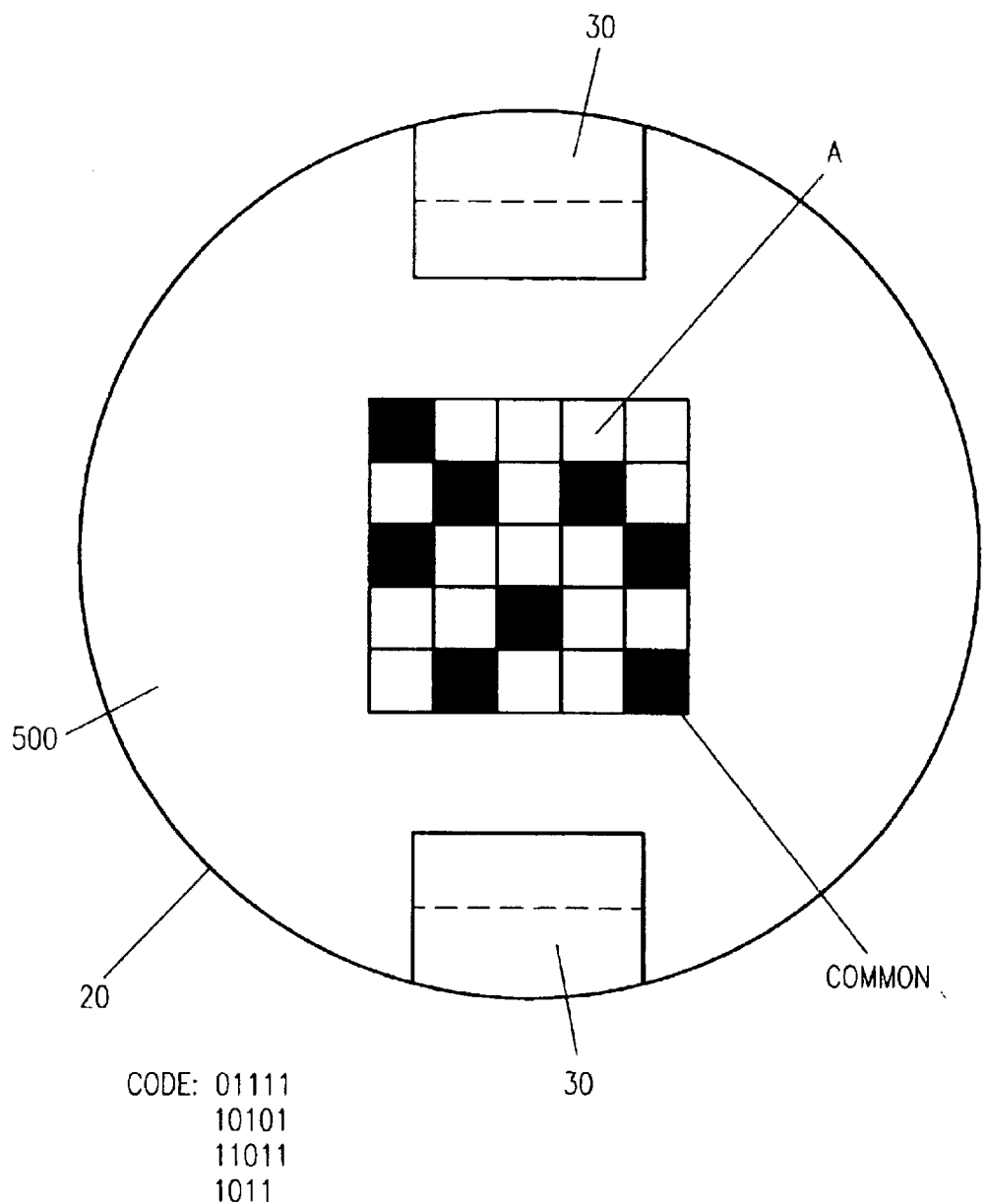
Figure 8A:
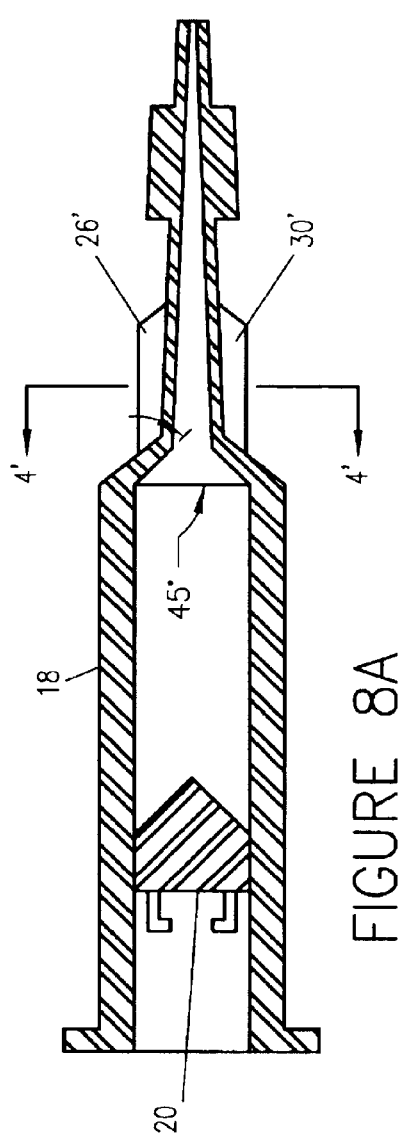
FIG. 8A illustrates a cross sectional view of a syringe incorporating alignment guides.
Figure 8E:
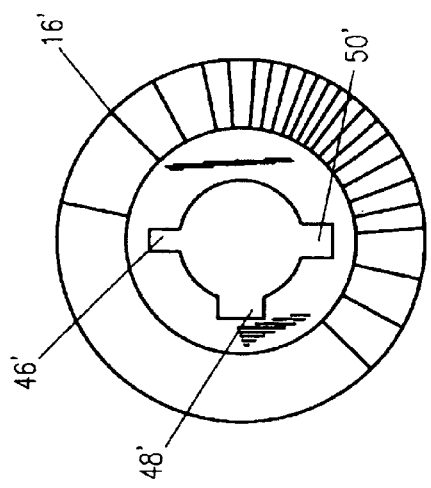
FIG. 8E illustrates a front view of the pressure jacket of FIG. 8D.
Figure 8C:
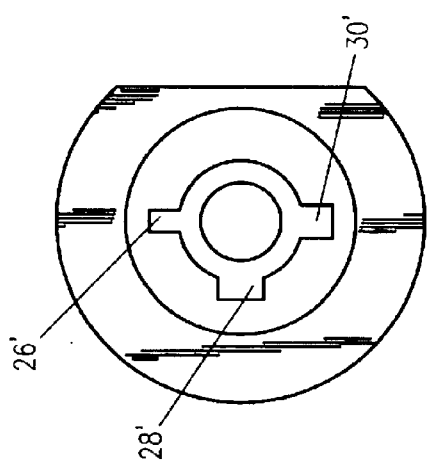
FIG. 8C illustrates a transverse cross-sectional view taken along line 4—4 of FIG. 8A.
Figure 8B:
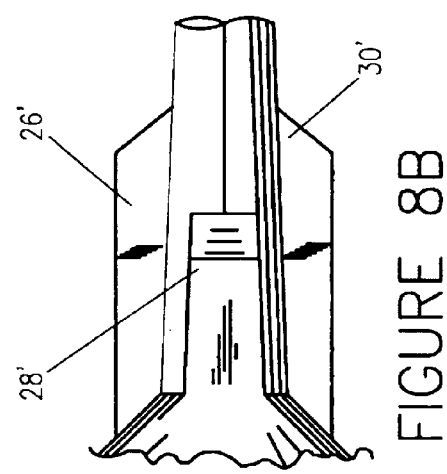
FIG. 8B illustrates a sectional plan view of the tapered neck region of the syringe of FIG. 8A.
Figure 8D:
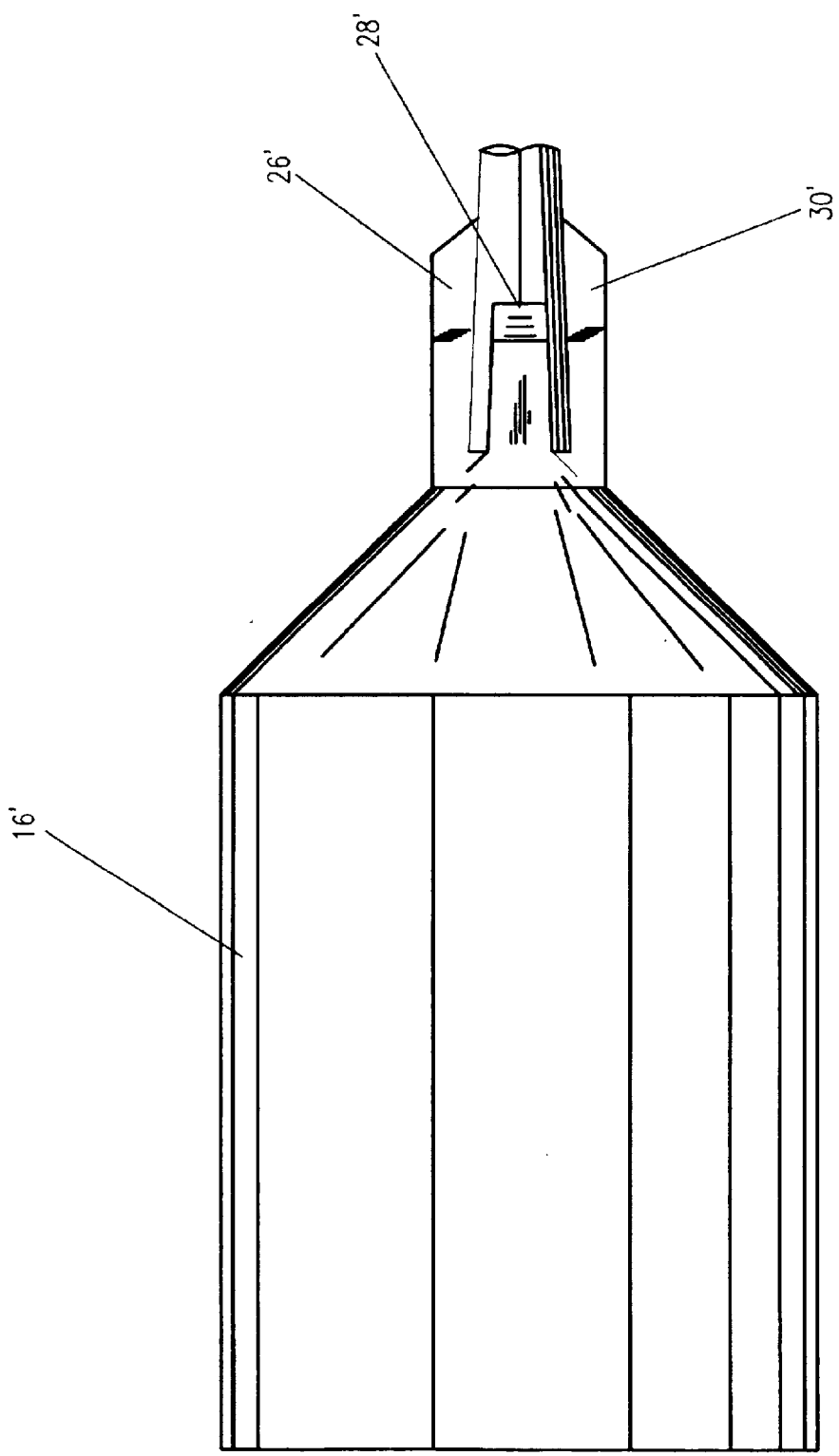
FIG. 8D illustrates a side view of a pressure jacket and syringe assembly incorporating an alignment path.

Other types of alignment are also possible. Present syringe plungers are identical if rotated 180° degrees. Using this property, the conductive elements could be separated into wedge shaped elements that are identical if rotated 180 degrees. FIG. 7A shows such a pattern that contains twice as much information (in the form of code contact members 50A, 50B–F, and 50B'–F' as the circular pattern of FIG. 3B. More wedges can be used to encode more information, if the rotational alignment can be guaranteed sufficiently well. This leads to the use of a two-dimensional information pattern. The information patterns need not be limited to wedges, but can include constant angle segments, enabling the outer elements to have more bits of information stored around their circumference. FIG. 7B shows an X-Y oriented two dimensional pattern that can also be used, but the regions nearer the axis A are more severely affected by any rotational misalignment. The example contains 25 code elements, and if one is used for the common contact, 24 bits of information can be encoded this way. Regions indicated in black are conductively connected.

Sufficient alignment can be ensured by having an alignment path from the readout elements, the injector head, the syringe mounting means, the syringe body, the plunger and the code elements on the plunger, similar to the alignment path described in U.S. Pat. No. 4,677,980 from the injector to the plunger attachment elements. Referring to FIGS. 8A through 8E, the tapered syringe neck of syringe 18' preferably includes guide extensions 26', 28' and 30' that slide into pressure jacket 16' (cooperating with guide extension notches or paths 46', 48' and 50', respectively) in only one orientation. Pressure jacket 16' is preferably mounted on the injector head with only one possible orientation, and by design the readout elements in, for example, the drive member (not shown in FIGS. 8A through 8E) are in a specific orientation. Also, during manufacture of syringe 18', plunger 20 is preferably inserted in the barrel of syringe 18' with its code elements (see, for example, FIG. 7B) oriented in a specific orientation with respect to guide extensions 26', 28' and 30'. This combination of design and controlled assembly provides for a syringe with an alignment path from guide members on the syringe through to the code elements, on the plunger in this example, that cooperates with an alignment path from the syringe mounting mechanism to the readout elements to enable the readout of a data rich code such as shown in FIG. 7B.

This alignment path is also advantageous if the code elements are placed elsewhere on syringe 18'. For example, the code elements can be placed on the guide extension 28'. In that embodiment, plunger 20 does not need to be part of the alignment path. If the code elements are placed elsewhere on syringe 18', for example, on the elongated body or barrel, an alignment path can also be readily created to facilitate alignment and readout by the readout elements.

For a syringe mounted as described in U.S. Pat. No. 5,383,858, the various retaining flanges on the syringe perform an alignment function because the flanges are rotated until they mate with the retaining flanges on the injector head. When the rotation stops, the syringe barrel is in a specific alignment with the injector head. If the injector head and syringe are designed and assembled as described above, the code elements will be in a specific alignment with the readout elements. As disclosed in U.S. Pat. No. 5,383,858, the syringe mounting operates equally well if the syringe is rotated 180°. If needed to enhance code density, the symmetry can be broken by making one flange larger than the other or by having multiple flanges in a non-symmetric arrangement. The more dense the encoding method (bits per area, length, degrees of rotation, etc.) the more repeatable and precise the alignment path from the readout elements to the code elements should preferably be.

The above embodiments describe contact made independent of any relative rotational motion between the code elements and the readout elements. The readout elements are moved straight into contact with the code elements. Or the readout is done after any relative translational motion is completed. Present syringes such as those described in U.S. Pat. No. 5,383,858 are rotated about their axis to attach them to the injector. Syringes like those described in U.S. Pat. No. 4,677,980 are translated or rotated about a different axis. This motion causes successive segments to make contact with a readout element or elements. As mentioned elsewhere, this "wiping" has the benefit of cleaning the contacts. In addition, the electronic control can sense the various conductive elements as they are moved over the readout elements. The electronic control device is preferably fast enough to debounce the successive contacts. This readout during motion is especially advantageous for other encoding methods described below such as magnetic and optical.

Figure 9A:
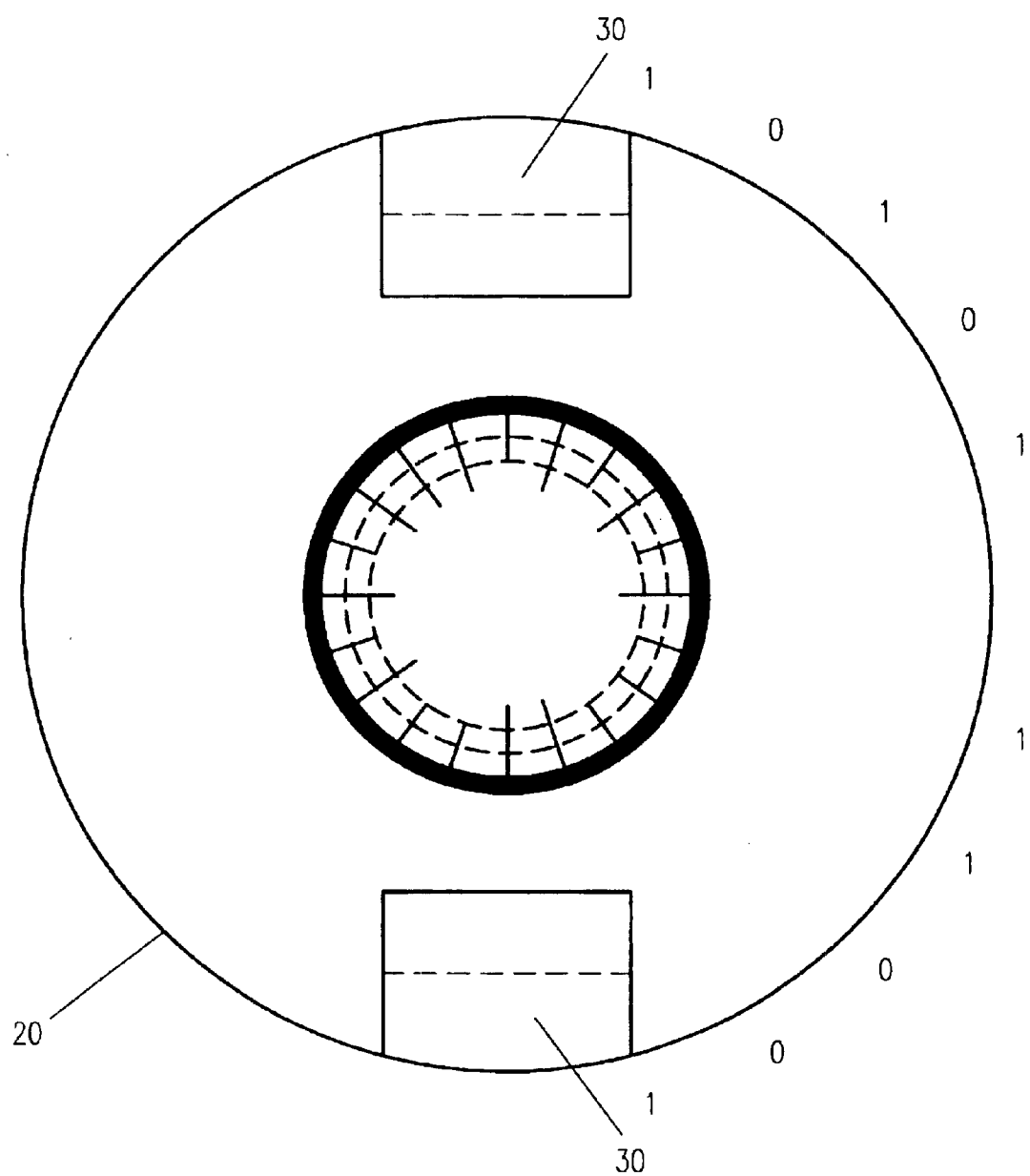
FIGS. 9A, 9B, and 9C illustrate encoding of a series of timing contacts and a series of data contacts for use during a "wiping" or scanning motion.

FIG. 9A illustrates one embodiment in which there is a radial array of code elements, all connected to an outer common contact 280. A readout element preferably contacts the common code element and holds it at ground. As the syringe is rotated, a first readout element travels a clock path 281 and a second readout element travels a data path 282. A circuit similar to that of FIG. 3A can be used. Every time the clock path readout element makes contact with a conductor on the code element, it is pulled low. At this time, electronic control device 65 observes the value of data path 282 readout element (after proper debouncing). If it is not connected to a code element, it will be high. If it is connected to a code element, it will be low. The pattern of FIG. 9A can be read with one data readout element if the syringe is rotated 180° or by two data readout elements 90° apart on path 282 if a 90° rotation is used.

Figure 9B:
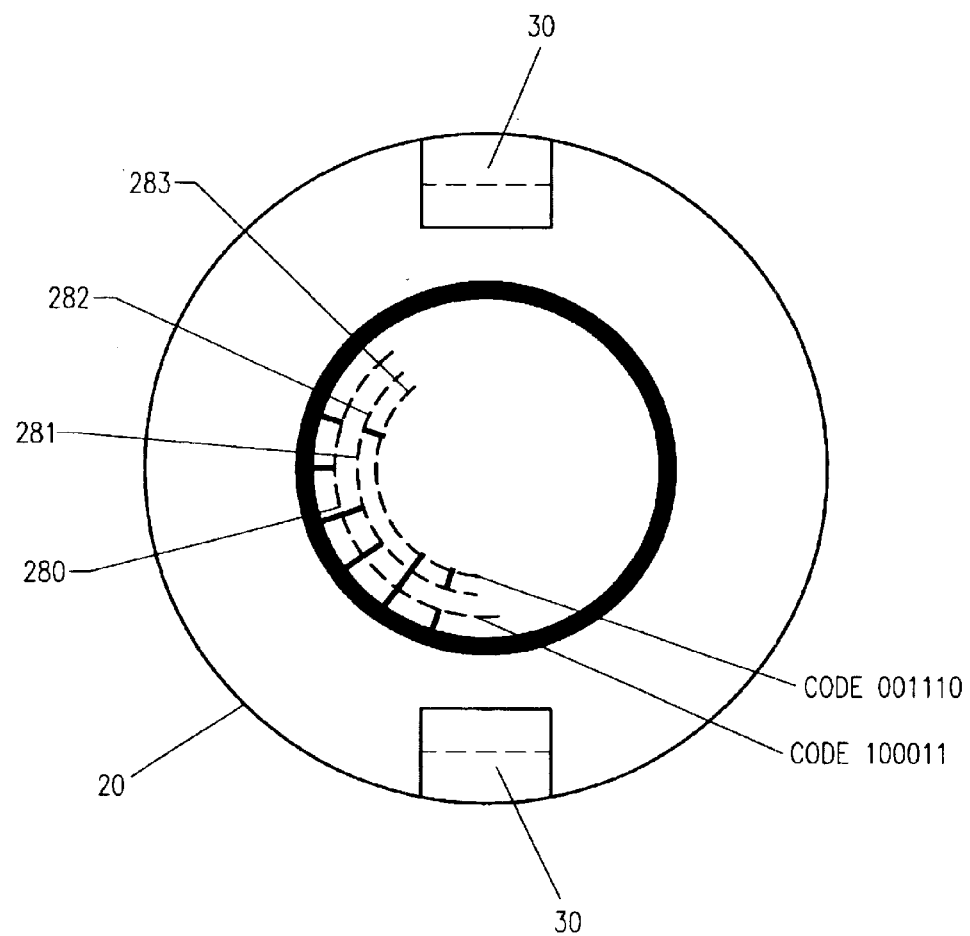
Figure 9C:
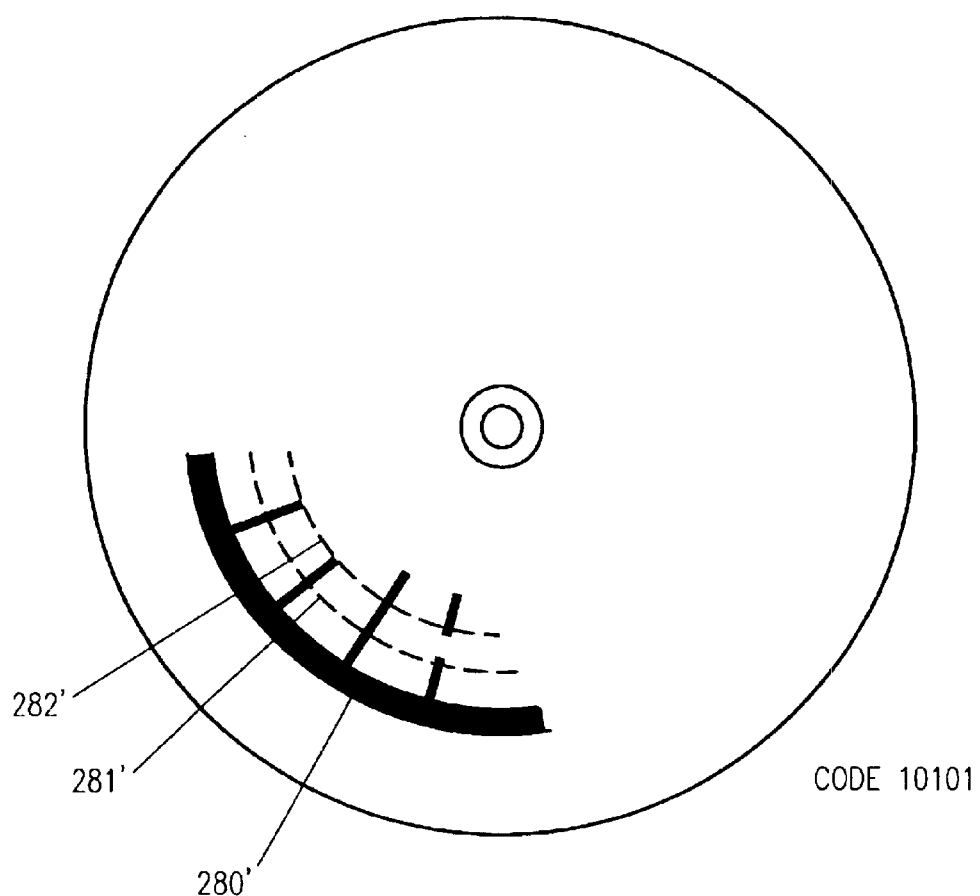

FIG. 9B illustrates a second data path 283 generally concentric to first data path 282 to achieve more data transfer. FIG. 9C illustrates a common contact 280', a clock path 281' and a data path 282' for a syringe mounted as described in U.S. Pat. No. 4,677,980. In this case the path the syringe plunger follows as it is installed is an arc about a center of rotation that is several inches from the syringe axis. In a similar fashion, any type of non-overlapping translational motion can be accommodated. (In the embodiment of FIGS. 9A through 9C, the contacts may alternatively be structured in one of many "self clocking" patterns known to those skilled in the art and the separate clock path readout element can be eliminated. Multiple data paths may be used in each embodiment.

In the embodiments described above, electrically conductive physical contact is made between conductive contact members in the syringe and corresponding conductive contact members in the powered injector to transmit information electrically encoded within the syringe (preferably in the plunger thereof) to a detection circuit in communicative connection with the powered injector. Coded information stored electronically in the syringe can also be transmitted to the powered injector without physical contact between the code and the reading or detection circuit. In such a case, energy is transmitted from the syringe to the detection circuit without requiring physical contact therebetween. In a preferred embodiment, information is transmitted from the syringe to the detection circuit via radio frequency (RF) energy.

Figure 10A:
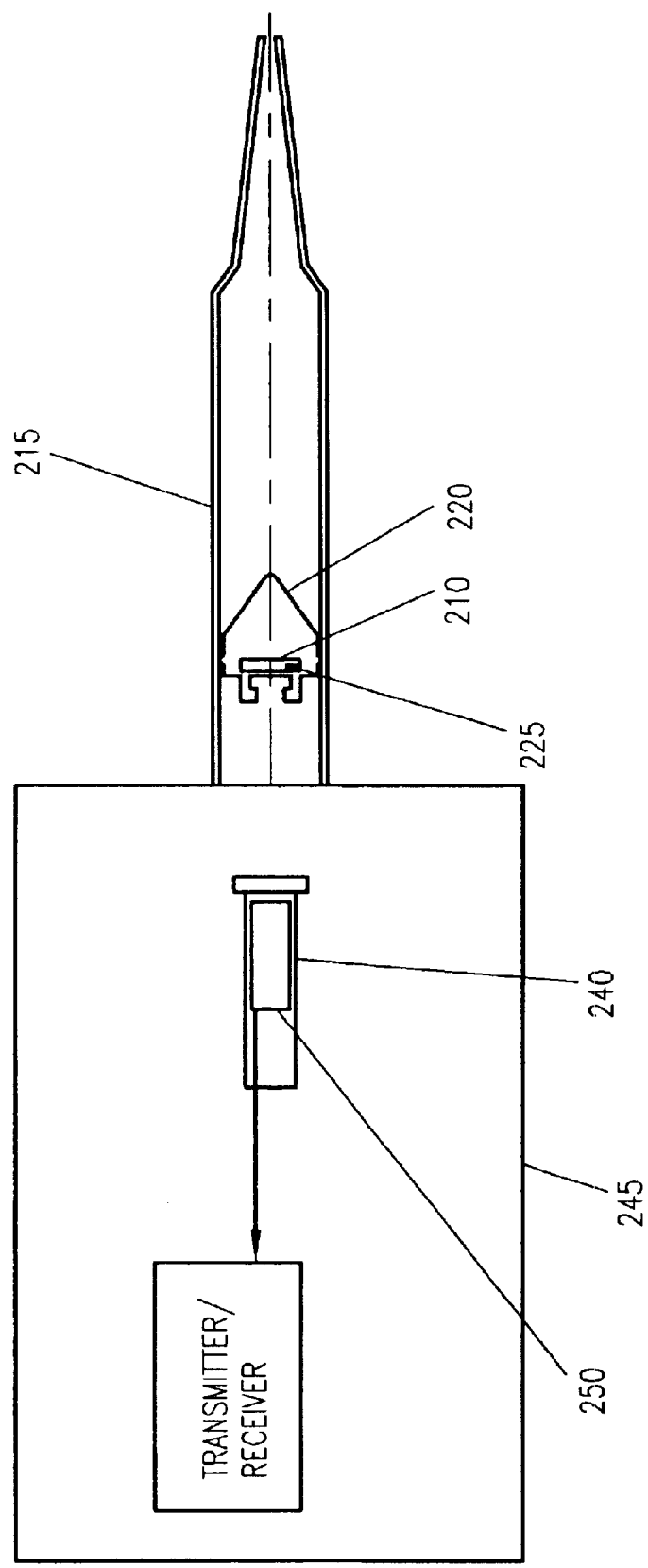
FIG. 10A illustrates a side cross-sectional view of another embodiment of an injector system of the present invention in which encoded information in the syringe is read by the injector in a non-contacting manner.

In a preferred embodiment as illustrated in FIG. 10A, a miniature RF transponder 210 is embedded in or attached to, for example, a plunger 220 of a syringe 215. Transponder 210 is preferably programmed with a code that is stored in an information storage unit 225 such as a semiconductor memory that is in operative connection with transponder 210. The code can be programmed into transponder 210 at nearly any time during or after the production process. An external RF field is preferably generated by a transmitter/receiver device preferably located in a powered injector 245. Preferably, the transmitter/receiver device comprises an antenna 250 placed in a drive member 240 (for example, a piston) of powered injector 245 as shown in FIG. 10A. Energy transmitted from the transmitter/receiver device via antenna 250 is received by transponder 210 which derives its power from the transmitted RF field. After transponder 210 derives sufficient power, it is stimulated to serially transmit the code stored in memory 210 as a frequency modulated signal to the transmitter/receiver device via antenna 240. Transponder and decoder systems of this type are available, for example, from Destron-Fearing, Inc., or from Texas Instruments, Inc. (under the TIRIS® trademark). These types of RF transponders work at distances up to 2 meters.

Another typical class of non-contacting RF identification methods encodes information on an information storage unit comprising a number of passive tuned circuits, each circuit representing a binary value in a digital code. These systems rely on the measurement of resonant RF response of the tuned circuits which are implemented as one or more printed circuits embedded in the syringe plunger.

Figure 10B:
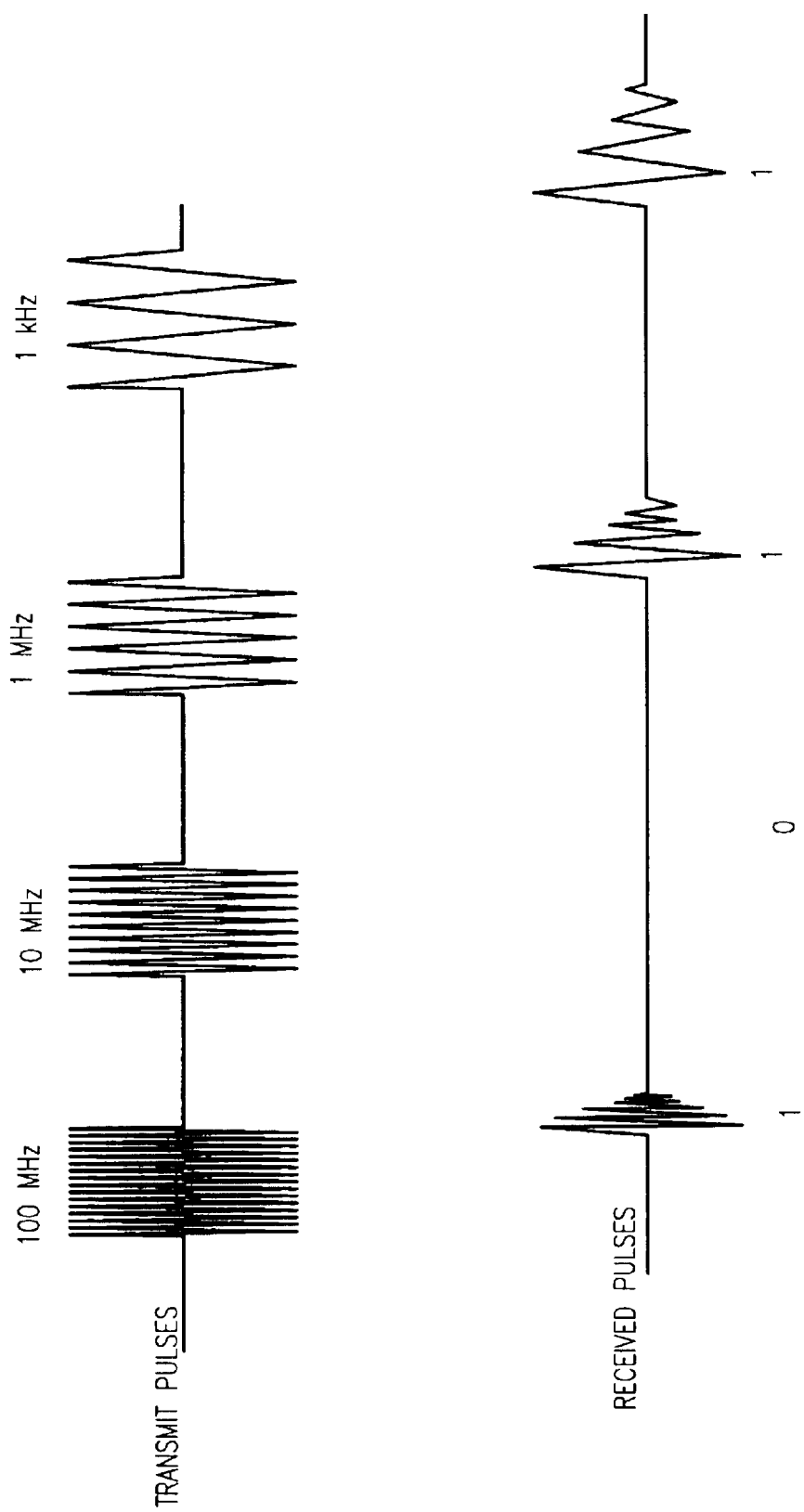
FIG. 10B illustrates an example of an RF signal produced by the plunger transponder of the injector system of FIG. 7A.

As illustrated in FIG. 10B, the transmitter/receiver device located in or in communication with powered injector 245 sends out a sequence of RF pulses whose frequency changes as a function of time over a specific frequency range. The encoding element is typically a tuned circuit that absorbs energy from the transmitted RF field at a specific frequency. Antenna 250 receives the energy radiated by the tuned circuits after the transmitter pulse is turned off. This mode of operation is somewhat similar to pulsed RF systems found in magnetic resonance imaging in which a transmit pulse is followed by an "echo" from the tuned circuit. When a tuned circuit is present, the echo response is initially strong, but decays as energy radiates into space. However, the echo is nonexistent if the tuned circuit is absent. Although it is possible to use separate transmit and receive antennae, a common practice is to use the same antenna for transmitting and receiving. The receiver is decoupled during the transmit pulse.

Tuned circuits can be formed in a variety of ways. One method known in the art uses conductive traces to form an inductor which is connected to a capacitor to form a resonant "tank" circuit. The resonant circuit stores energy of the correct frequency during the transmit pulse and then gives the energy back to the receiver as a decaying waveform of the same frequency. Harmonics of the fundamental frequency are usually removed by filters in the receiver.

Several such resonant circuits can be fabricated on a printed circuit board to implement a binary code. However, the coupling between the multiple resonant circuits becomes a problem as the number of such circuits increases. In that regard, each circuit becomes "detuned away from resonance" as a result of the influence of the other circuits. Since coupling between the several circuits is undesirable, care is preferably taken to separate the resonant frequencies far enough apart to minimize mutual coupling between them. This result is achieved by properly selecting the capacitor values or by physically spacing the circuits far enough apart.

FIG. 10B illustrates a typical sequence of transmitted and received pulses from a circuit board containing resonant circuits at 100 megahertz (MHz), 1 MHz, and 100 Kilohertz. The resonant frequencies are preferably set apart by factors of 10 to reduce undesirable coupling among the resonant circuits which tends to detune them. In this embodiment, the resonant circuit for 10 MHz is missing, so there is no received response for the 10 MHz pulse. Therefore, the binary code implemented is "1011".

The non-contacting measurement of impedance discussed above in reference to a resonant circuit can be utilized to measure resistance, capacitance, inductance, zener voltage or other impedances. The difference from earlier impedance measuring embodiments is that when there is not a direct current electric path, the electrical energy is either coupled capacitively or inductively. To an extent, these couplings are sensitive to the distance between the coupling members and so generally require close proximity (capacitive coupling more than inductive coupling.) However, by measuring the ratios of impedance elements $Z_1$, $Z_2$, and $Z_3$, this distance sensitivity can be overcome.

While the information storage units, such as the transponder 210 and the tuned circuits discussed above, may be disposed on or embedded in the plunger 220 of a syringe 215, it is also specifically contemplated that the information storage units may be positioned on the syringe body, within the packaging containing the syringe 251 or in any suitable location from where the syringe configuration information can be conveyed to the detector associated with the injector.

For high pressure injectors the connection between the plunger and the drive means should be robust and tight. Thus this location/interface is a good place for the transfer of coded information. There are other methods of encoding information that can be utilized at the plunger/drive member interface. One alternative is an optical code. An optical readout integrated circuit can be placed at the end of the drive member or it can, for example, be located remotely and be coupled to the plunger/drive member interface with optical fiber. A linear array of simple phototransistors can be used with an optical pattern of, for example, concentric rings as shown in FIG. 3B. A benefit of optical readout is the elimination of the common contact. Optical readout can also be used to sense proximity of the drive means to the plunger. With a two-dimensional optical readout device of sufficient resolution, alignment can be modified in the microprocessor after reading, thereby making alignment less critical and enabling more sophisticated data encoding. Character recognition is even possible. The optical code can, for example, use simple absorption-reflection differences, fluorescence or other methods known in the art. Any type of convenient electromagnetic radiation can be used, including infrared, visible, or ultraviolet.

Various magnetic encoding elements can also be utilized. The simplest is the presence or absence of magnetic material at specific locations. Concentric rings of steel can, for example, be present or absent at specific locations. The readout mechanism may be small inductive coils or hall effect sensors instead of contacting pins. Permanent magnetic elements may be incorporated into the plunger. Magnetostrictive elements may alternatively be employed. Magnetic inks may be printed onto the plunger or plastic patterns using magnetic particles mixed into the plastic. Suitable readout elements include, for example, coils, hall effect sensors, Kerr effect sensors, and resonant circuit whose resonant frequency is shifted by the presence of the magnetic material.

The surface of the plunger can include physical indicia that are pressed against the drive element when placed in operating position. Among these indicia are bumps, divots, ridges, or trenches. The physical indicia are preferably read by switches or piezoelectric material with patterned contacts. These indicia can alternatively be read by force sensors, or an optical sensor(s). Again, rotationally symmetric methods such as concentric rings (similar to those shown in FIG. 3B) are preferred because of the tolerance to rotational positioning. With the alignment path discussed above, however, a more sophisticated pattern can be used.

Ultrasonic resonators are another alternative. A number of such resonators can be incorporated in the plunger. The operation of ultrasonic resonators is similar to the electronic resonators described above and shown in FIGS. 10A and 10B, except that the energy transmitted and received is sound energy of a specific frequency rather than electrical energy.

A variety of encoding elements have been described above. Some encoding elements can be read by multiple types of readout elements. Or, multiple types of encoding elements can be used sequentially or simultaneously. This has the benefit of flexibility for the designer. It can also provide redundancy of readout. A third benefit is that one readout method may be used to determine timing during a scanned readout while a second method is used for actual data readout. A fourth benefit is that one method may be used for detecting plunger—drive element proximity while a second method is used for data readout. For instance, a metal disc with selectively placed insulating rings can be read out through direct contact or optically, if the rings are absorptive to the wavelength used and the metal is reflective. Other combinations are also possible.

As mentioned above, intimate contact is made between the plunger and the drive member. However, because of this intimate contact, there are other functions that may be accomplished at the piston/drive member interface. Because of such other functions or uses, it may be necessary to place the code elements and readout elsewhere in relation to the syringe to free up the plunger/drive member interface.

Figure 11:
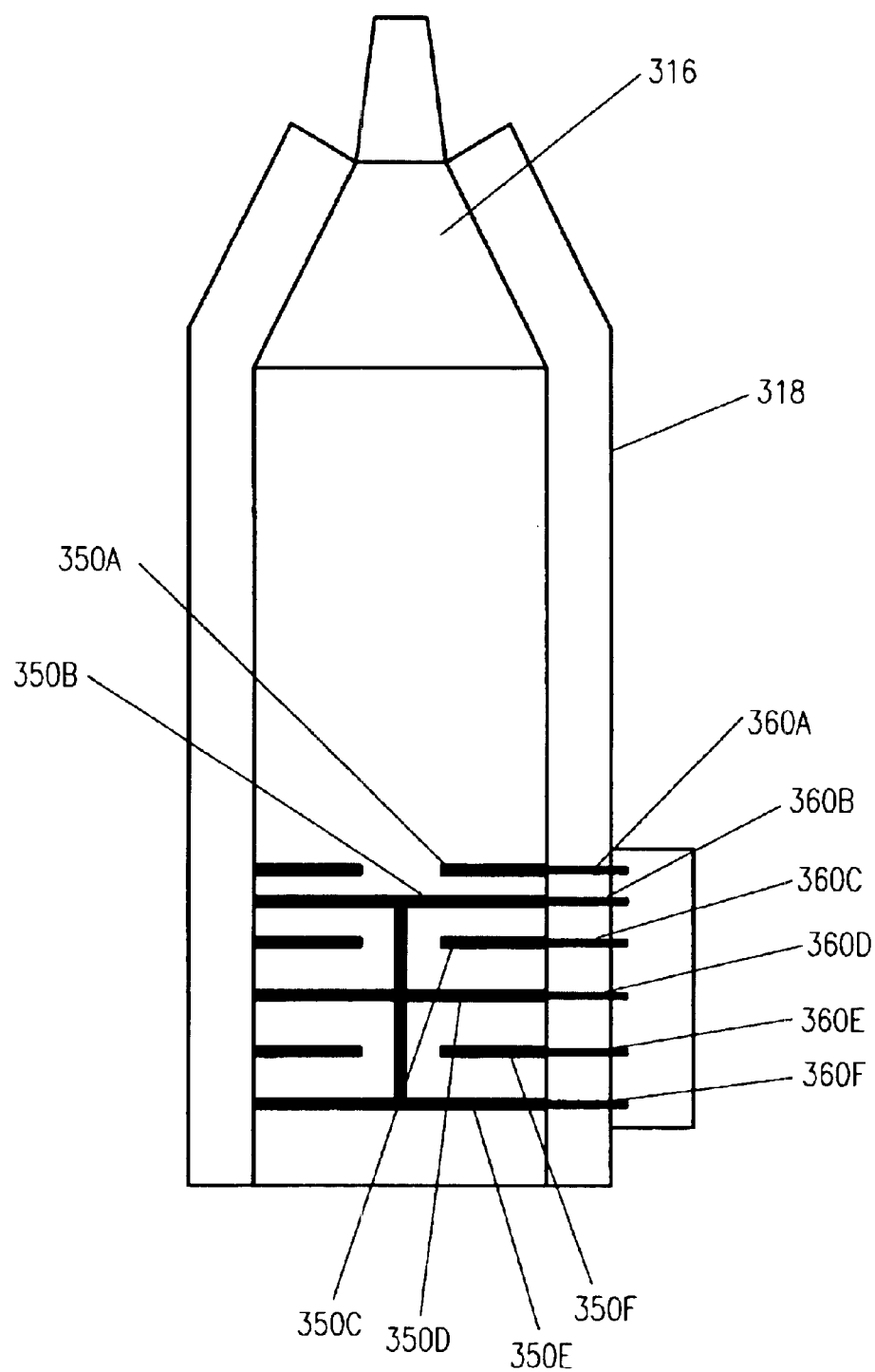
FIG. 11 illustrates an example of information encoded on a syringe to be read through the pressure jacket.

In an embodiment illustrated in FIG. 11, information is communicated via a pressure jacket 318. Pressure jacket 318 is typically a robust, generally cylindrical element that enables a relatively thin-walled syringe 316 to be used at high pressures. Pressure jackets are described in U.S. Pat. Nos. 4,006,736 and 4,667,980. Readout pins 360A–D can, for example, form a linear array at different axial positions near the back of pressure jacket 318. Code elements 350A–D can, for example, be formed as circumferential bands around the outside of the elongated body or barrel of syringe 316. Many of the other exemplary encoding and readout methods described above can be applied to this location as well.

Figure 12:
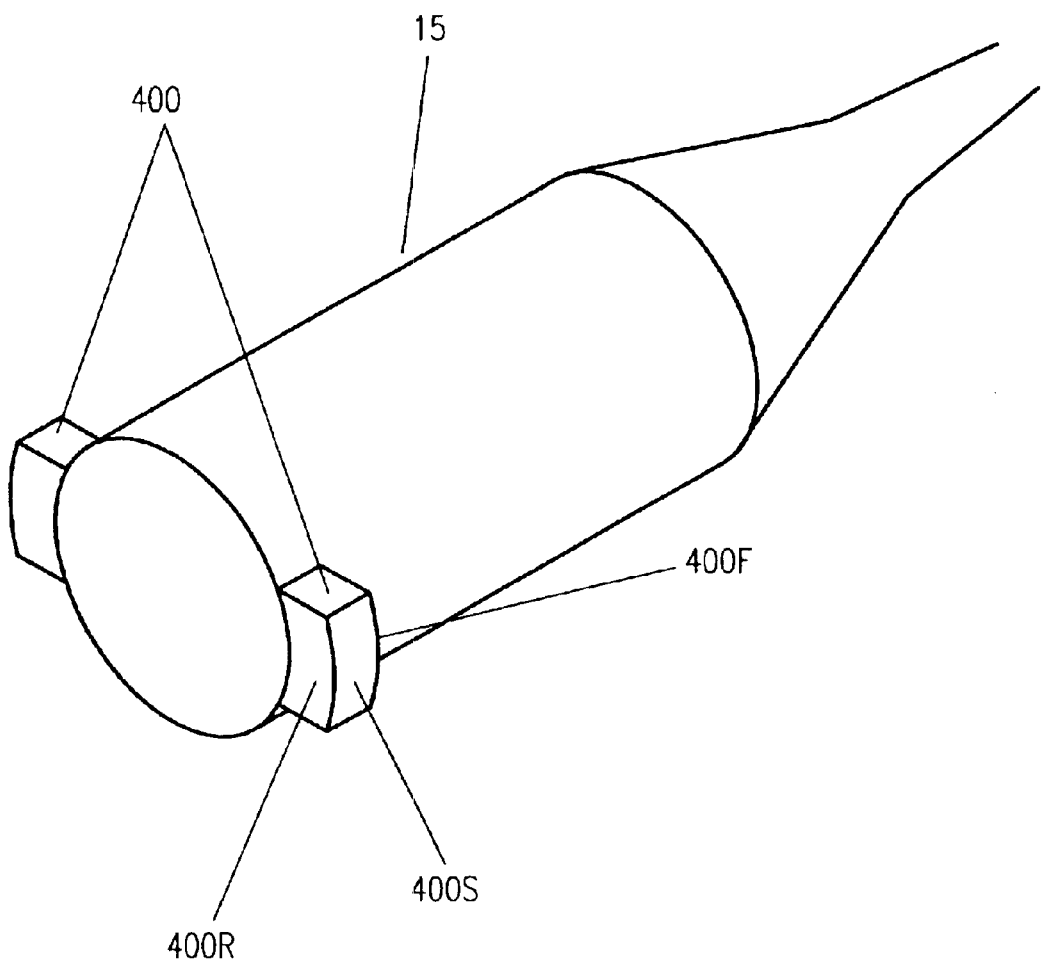
FIG. 12 illustrates various locations for mounting encoded information with respect to syringe mounting flanges.

Another location that can be advantageously used for contacting readouts is the syringe mounting flange for those syringes (described, for example, in U.S. Pat. No. 5,383,858) that do not employ pressure jackets. U.S. Pat. No. 5,383,858 describes bar codes or physical indicia in the region just ahead of the mounting flange of the syringe thereof. FIG. 12 illustrates selected aspects of the syringe. In a commercially available injector, the Envision™ available from Medrad, Inc., physical indicia (depressions) on the back 400R of the syringe mounting flange 400 are used as code elements. Those physical indicia/depressions are sensed by pins that are depressed or not depressed depending upon the presence or absence of the physical indicia. Applying the various code elements discussed earlier in this patent to the mounting flange provides an improved alternative with higher code density than currently available. The readout elements, pins in this embodiment, can be mounted in the injector head to contact conductive code elements mounted on back surface 400R of syringe mounting flange 400. In this case, the readout pins are preferably arranged circumferrentially and the code elements are arranged axially. It is also possible to place the code on front surface 400F of mounting flange 400 or on outer circumferential surface 400S thereof. If non-contacting methods are used, the circuit can be mounted in the flange.

Figure 13A:
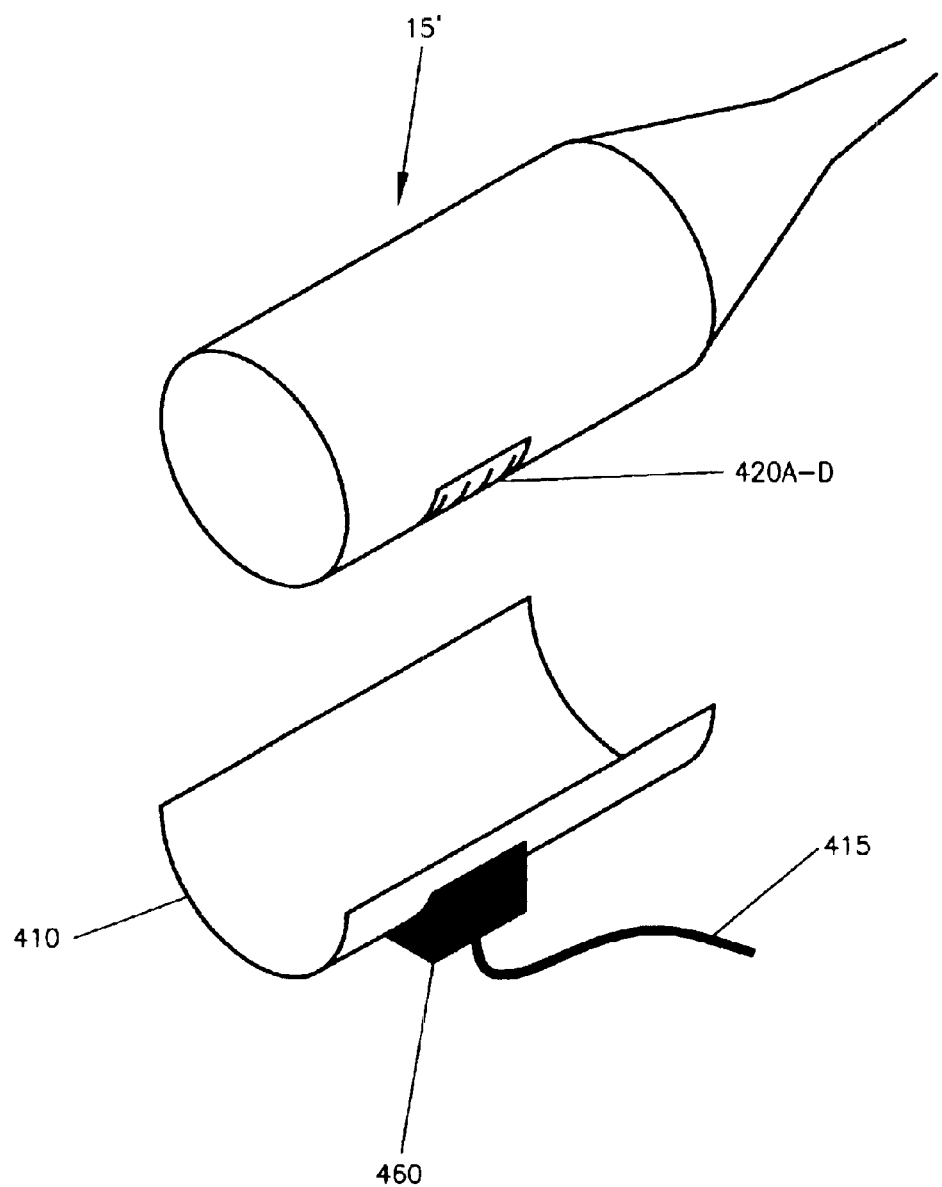
FIGS. 13A and 13B illustrate encoding elements on a syringe barrel and readout elements on a syringe heater that mates with the syringe barrel.
Figure 13B:
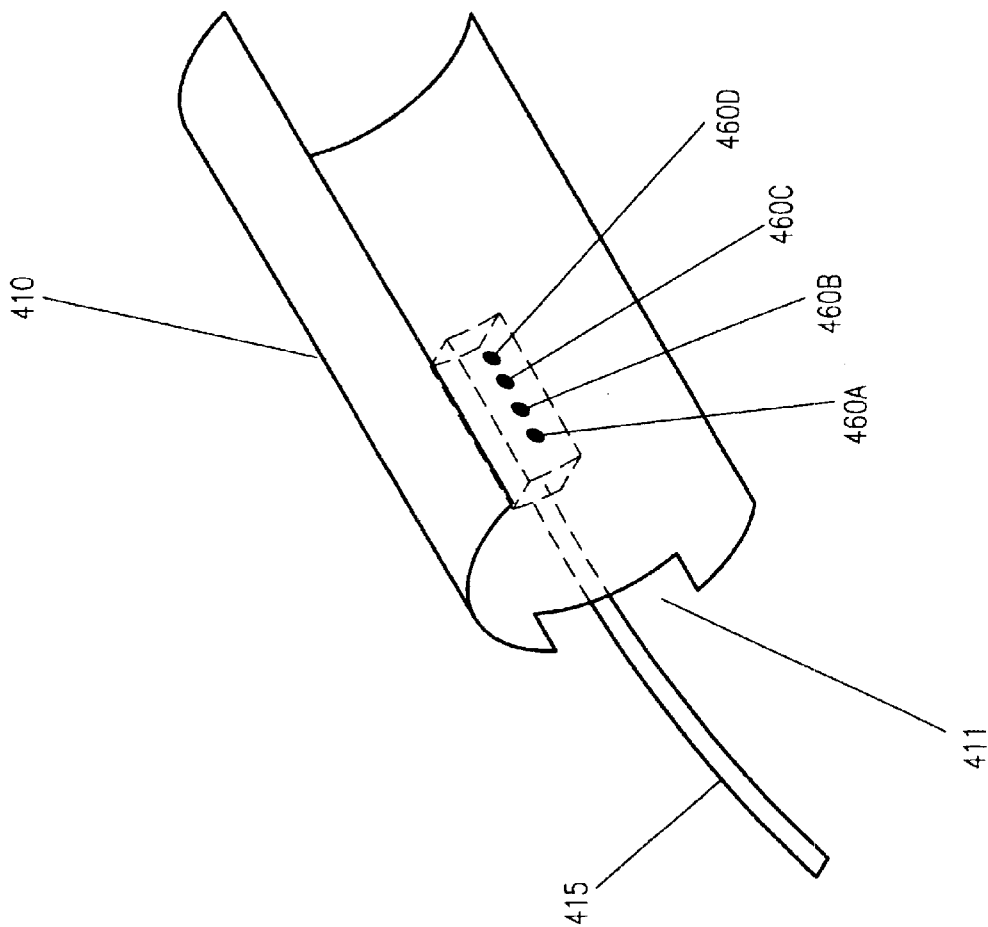

FIGS. 13A and 13B illustrate a heater jacket 410 that is placed against a syringe 15' to heat it. Encoding elements 420A through 420D can be placed, for example, on the side of syringe 15' and the readout elements 460A through 460D, can be positioned on syringe heater 410. Readout contact or elements 460A–D contact code contacts or elements 420A–D when syringe heater 410 is in position. The code information can be communicated to the electronic control device (not shown) through, for example, a wiring harness 415. In this embodiment an alignment path is provided by guide member 412 on the syringe mating with slot member 411 on the syringe heater. When the two are fully engaged, the readout elements 460A–D are contacting the code elements 420A–D. This is an example of an alignment path that does not go through the injector. In this case, it is from the code elements to the syringe, to the syringe guide member 412, to the readout elements' physical support 410 via slot 411, to the readout elements themselves. The simplest alignment path would be readout elements directly to code elements. This result can be accomplished, for example, if the readout elements themselves are pins that fit into corresponding holes in the code elements. If the readout elements are not properly mated to the holes, no code or an error code would be read, or the readout element would not stay in position or could not physically be put into position.

In general, the methods disclosed herein can be placed in many other locations in relationship to the syringe. An injector commercially available from Liebel Flarsheim (and described in PCT publication WO98/22168) uses a device to look for air in the neck of the syringe. Because it is in consistent repeatable contact with the syringe, readout elements using any of the methods described herein could be positioned in or adjacent to the air detector. Specifically, circumferential rings could be the code elements which are read either electrically or optically.

Figure 14:
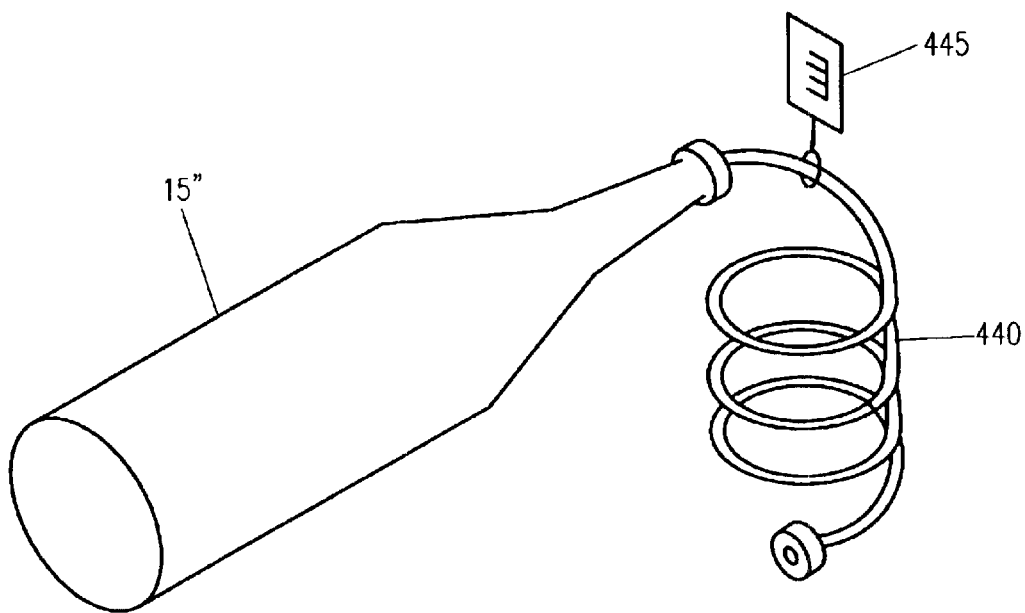
FIG. 14 illustrates encoding elements associated with an attached fluid path element.

In addition, some syringes are now provided with additional fluid path elements either preconnected or packaged with the syringe as illustrated in FIG. 14. Currently, such fluid path elements include connector tubes 440 and one way valves. Encoding elements 445 can be associated with such additional fluid path elements rather than with syringe 15" and can include information about the presence or properties (such as pressure limit) of the associated fluid path elements and/or syringe 15" with which the fluid path elements are packaged. The encoding elements can be as simple as bar coded label that is read by swiping it over a bar code reader on the injector head. Alternatively, one of the remote reading tags described above can be used.

There is a cost reduction (although ease of use may is also decrease) in having the code element(s) of the present invention separate from the plunger but associated with it in use. As described above, an encoded attachment element or cap (having, for example, a rear surface 500 as illustrated in FIG. 7B) can be fit onto the plunger or onto the drive member via an attachment mechanism such as a snap fit as known in the art. The cap includes the code elements for the encoding method chosen. One cap may be associated with a number of syringes, or one cap may be associated with only a single syringe. Such a cap may be placed onto the drive element or the plunger before installing the syringe onto the injector.

The cap can be generalized to represent a separate encoding element that is associated with one or more syringes and is used to convey to the injector information that is common to all the syringes. In one embodiment, both a cap (a common data element) and custom encoded syringe data, can be used in combination. For example the cap can have holes that let some readout element pins contact the syringe code elements while other readout element pins contact those elements in the cap. The cap can use any of the encoding-readout mechanisms/methods disclosed herein. Similar "caps" (that is, attachment elements) can be used to convey coded information to all of the places readout elements can be placed.

There are a number of times at which the information can be encoded into the code elements of the present invention. For example, information can be encoded:

When the Plunger (or Syringe Barrel) is First Manufactured: for example, by insert molding a conductor or molded in physical indicia.

When the Parts are Assembled into a Syringe: for example, by breaking off metal pieces, drilling physical indicia, inserting a printed circuit board, or opening fuses.

When the Syringe is Filled: for example, by the methods described above.

After Sterilization: for example, by the methods described above.

When Shipped: for example, by inserting an encoded cap or similar attachment element into the box.

At the End User Site: this is most easily done with an electronic means such as EPROM or EEPROM. It can also be done with magnetic, fusible, impedance, or any of the disclosed methods that can be modified at the user site. If the syringe is filled at the user site, information about the contents could be added here, for example using a bar coded label.

When Installed in the Injector: (same as previous).

After Use: Such timing of encoding can be used to prevent reuse or to encode usage information to be returned to the hospital pharmacy or the supplier. For example, a tab can be broken off as the syringe is removed. This change in encoding is preferably readable if the operator tried to reinstall the used syringe. Alternatively, a fuse can be opened after use. Other methods of encoding as described above can also be used.

In addition to providing syringe configuration information to a powered injector, the present invention may be used to generate and maintain data records associated with injection procedures. For example, to update inventory control records and to satisfy medical and insurance billing and cost information requirements, records of information, such as the type of syringe used, the amount of contrast medium used, the type of contrast medium used, the sterilization date, the expiration date, lot codes, the properties of the contrast media, and/or other clinically relevant information, may be generated and maintained for use by, for example, external billing, inventory or control computer systems.

In a preferred embodiment, a hospital or vendor computer system may be interfaced with the injector via an access port to access and process syringe configuration information for billing, insurance, inventory and/or patient record-keeping purposes.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An encoded element for use with a syringe and an injector in communication with a detector comprising a plurality of electrically conductive readout contact members, the encoded element comprising: an attachment mechanism adapted to detachably connect the encoded element to a plunger of the syringe or a drive member of the injector; and a storage system comprising a plurality of electrically conductive code contact members, the storage system being operable to store encoded syringe information readable by the detector when the syringe is engaged with the injector and to convey the syringe information to the detector when contact is made between the storage system and the detector.

2. The encoded element of claim 1 wherein the plurality of code contact members is in communication with a memory, the memory being readable by the detector.

3. The encoded element of claim 2 wherein the memory is a ROM, an EPROM or an EEPROM memory.

4. The encoded element of claim 1 wherein the position of the plunger within the syringe is determined when the storage system contacts the detector.

5. The encoded element of claim 1 wherein the attachment mechanism is adapted to detachably connect the encoded element to the plunger of the syringe.

6. A syringe for use with a powered injector comprising a drive member and a detector, the syringe comprising:
an elongated body;
a plunger slidably disposed within the elongated body and operable to be driven by the drive member to inject a fluid into a patient; and
a member adapted to be connected to the plunger, the member comprising a mechanism for detachably connecting the member to the plunger and an information storage system operable to convey syringe information to the detector when contact is made between the information storage system and the detector, wherein the position of the plunger within the syringe is determined when the information storage system contacts the detector.

7. The syringe of claim 6 wherein the information storage system comprises at least one electrically conductive code contact member and the detector comprises at least one electrically conductive readout contact member.

8. The syringe of claim 7 wherein the at least one code contact member comprises a plurality of code contact members.

9. The syringe of claim 7 wherein the at least one code contact member is in communication with a memory, the memory being readable by the detector.

10. The syringe of claim 9 wherein the memory is a ROM, an EPROM or an EEPROM memory.

11. A syringe for use with a powered injector comprising a drive member and a detector comprising at least one electrically conductive readout contact member, the syringe comprising:
an elongated body;
a plunger slidably disposed within the elongated body and operable to be driven by the drive member to inject a fluid into a patient; and
a member adapted to be connected to the plunger, the member comprising a mechanism for connecting the member to the plunger and an information storage system operable to convey syringe information to the detector when contact is made between the information storage system and the detector, the information storage system comprising a plurality of electrically conductive code contact members in communication with a ROM, an EPROM or an EEPROM memory, the memory being readable by the detector.

12. The syringe of claim 11 wherein the position of the plunger within the syringe is determined when the information storage system contacts the detector.

13. The syringe of claim 11 wherein the connection mechanism of the member is adapted to detachably connect the member to the plunger of the syringe.

14. An encoded element for use with a syringe and an injector in communication with a detector, the encoded element comprising: an attachment mechanism adapted to detachably connect the encoded element to a plunger of the syringe or a drive member of the injector; and a storage system operable to store encoded syringe information readable by the detector when the syringe is engaged with the injector, wherein the position of the plunger within the syringe is determined when the storage system contacts the detector.

15. The encoded element of claim 14 wherein the storage system is operable to convey syringe information to the detector when contact is made between the storage system and the detector.

16. The encoded element of claim 15 wherein the storage system comprises at least one electrically conductive code contact member and the detector comprises at least one electrically conductive readout contact member.

17. The encoded element of claim 16 wherein the at least one code contact member comprises a plurality of code contact members.

18. The encoded element of claim 16 wherein the at least one code contact member is in communication with a memory, the memory being readable by the detector.

19. The encoded element of claim 18 wherein the memory is a ROM, an EPROM or an EEPROM memory.

20. An encoded element for use with a syringe and an injector in communication with a detector, the encoded element comprising: an attachment mechanism adapted to detachably connect the encoded element to a plunger of the syringe or a drive member of the injector; and a storage system comprising a plurality of tuned circuits operable to store encoded syringe information readable by the detector when the syringe is engaged with the injector, wherein the storage system is operable to convey syringe information to the detector without physical contact being made between the storage system and the detector.

21. The encoded element of claim 20 wherein the tuned circuits comprise resonant circuits.

22. The encoded element of claim 21 wherein the tuned circuits are disposed on a printed circuit board.

* * * * *